(12) United States Patent
Morgan et al.

(10) Patent No.: US 9,771,554 B2
(45) Date of Patent: Sep. 26, 2017

(54) DEVICE AND METHOD FOR ENGINEERING LIVING TISSUES

(71) Applicants: Brown University, Providence, RI (US); Rhode Island Hospital, Providence, RI (US)

(72) Inventors: Jeffrey R. Morgan, Providence, RI (US); Andrew Blakely, Providence, RI (US); John Murphy, Providence, RI (US); Anubhav Tripathi, Providence, RI (US); William Patterson, Providence, RI (US)

(73) Assignees: Brown University, Providence, RI (US); Rhode Island Hospital, Providence, RI (US)

( * ) Notice: Subject to any disclaimer, the term of this patent is extended or adjusted under 35 U.S.C. 154(b) by 313 days.

(21) Appl. No.: 14/328,956

(22) Filed: Jul. 11, 2014

(65) Prior Publication Data

US 2015/0024495 A1  Jan. 22, 2015

Related U.S. Application Data

(60) Provisional application No. 61/846,703, filed on Jul. 16, 2013.

(51) Int. Cl.
| | |
|---|---|
| *C12N 5/00* | (2006.01) |
| *C12M 3/00* | (2006.01) |
| *C12M 1/12* | (2006.01) |
| *C12M 1/00* | (2006.01) |

(52) U.S. Cl.
CPC ........... *C12N 5/0068* (2013.01); *C12M 21/08* (2013.01); *C12M 25/02* (2013.01); *C12M 29/10* (2013.01); *C12N 5/0062* (2013.01); *C12N 2513/00* (2013.01); *C12N 2533/76* (2013.01)

(58) Field of Classification Search
CPC ....................................................... C12M 21/08
See application file for complete search history.

(56) References Cited

U.S. PATENT DOCUMENTS

| | | | | |
|---|---|---|---|---|
| 2005/0026221 | A1* | 2/2005 | Richmond | B01L 3/021 435/7.2 |
| 2011/0200559 | A1* | 8/2011 | Koga | A61L 27/3843 424/93.1 |

OTHER PUBLICATIONS

Tejavibulya, N., Youssef, J., Bao, B., Ferruccio, T-M and Morgan, J.R. Directed Self-Assembly of Large Scaffold-free Multi-cellular Honeycomb Structures. *Biofabrication* 3, 1-9, 2011.

(Continued)

*Primary Examiner* — Jonathan Hurst
(74) *Attorney, Agent, or Firm* — Hamilton, Brook, Smith & Reynolds, P.C.

(57) ABSTRACT

A device for assembling aggregations of adherent cells includes a gripper moveable within an assembly vessel that fixes aggregations of adherent cells at a membrane of the gripper and, by movement of the gripper, assembles aggregations of cells on a separate membrane within the vessel, thereby creating a three-dimensional assembly of aggregations of cells that fuse and can be employed in surgical procedures as a unitary tissue of adherent cells. The aggregations of cells, as assembled, can assume three-dimensional configurations distinct from any one of the component aggregations of cells assembled.

17 Claims, 28 Drawing Sheets
(10 of 28 Drawing Sheet(s) Filed in Color)

(56) References Cited

OTHER PUBLICATIONS

Livoti, C.M., and Morgan, J.R. Self-Assembly and Tissue Fusion of Toroid-Shaped Minimal Building Units. *Tissue Eng.* 16: 2051-2061, 2010.

Boland, T., Mironov V, Gutowska A, Roth EA, Markwald RR. Cell and organ printing 2: fusion of cell aggregates in three-dimensional gels. *Anat Rec A Discov Mol Cell Evol Biol.* 272(2): 497-502, 2003.

Mironov, V., T. Boland, T. Trusk, G. Forgacs, and R.R. Markwald. Organ printing: computer-aided jet-based 3D tissue engineering. *Trends Biotechnol.* 21(4): 157-61, 2003.

Smith C. M., Stone, A.L., Parkhill, R. L., Stewart, R.L., Simpkins, M.W., Kachurin, A.M., Warren, W.L. and Williams, S.K. Three-dimensional bioassembly tool for generating viable tissue-engineered constructs. *Tissue Eng.* 10 1566-76, 2004.

Xu, T., Jin, J., Gregory, C., Hickman, J.J. and Boland, T. Inkjet printing of viable mammalian cells. *Biomaterials* 26 93-9, 2005.

Nakamura, M., Kobayashi, A., Takagi, F., Watanabe, A., Hiruma, Y., Ohuchi, K., Iwasaki, Y., Horie, M., Morita, I. and Takatani, S. Biocompatible inkjet printing technique for designed seeding of individual living cells. *Tissue Eng.* 11 1658-66, 2005.

Boland, T., Xu, T., Damon, B. and Cui, X. Application of inkjet printing to tissue engineering *Biotech. J.* 1 910-7, 2006.

Xu, T., Gregory, C. A., Molnar, P., Cui, X., Jalota, S., Bhaduri, S.B. and Boland. T. Viability and electrophysiology of neural cell structures generated by the inkjet printing method. *Biomaterials* 27 3580-8, 2006.

Campbell, P.G. and Weiss, L.E. Tissue engineering with the aid of inkjet printers *Expert Opin. Biol. Ther.* 7 1123-7, 2007.

Smith, C. M., Christian, J. J., Warren, W. L. and Williams, S. K. Characterizing environmental factors that impact the viability of tissue-engineered constructs fabricated by a direct-write bioassembly tool *Tissue Eng.* 13 373-83, 2007.

Phillippi J A, Miller E, Weiss L, Huard J, Waggoner A and Campbell P. Microenvironments engineered by inkjet bioprinting spatially direct adult stem cells toward muscle- and bone-like subpopulations *Stem Cells* 26 127-34, 2008.

Saunders R E, Gough J E and Derby B. Delivery of human fibroblast cells by piezoelectric drop-on-demand inkjet printing *Biomaterials* 29, 193-203, 2008.

Mironov, V., Visconti, R.P., Kasyanov, V., Forgacs, G., Drake, C.J. Markwald, R.R. Organ printing: tissue spheroids as building blocks. *Biomaterials* 30(12): p. 2164-74, 2009.

Nishiyama Y, Nakamura M, Henmi C, Yamaguchi K, Mochizuki S, Nakagawa H and Takiura K. Development of a three-dimensional bioprinter: construction of cell supporting structures using hydrogel and state-of-the-art inkjet technology *J. Biomech. Eng.* 131 035001, 2009.

Yamazoe H and Tanabe T. Cell micropatterning on an albumin-based substrate using an inkjet printing technique J. Biomed. Mater. Res. A 91 1202-9, 2009.

Jakab, K., Norotte, C., Marga, F., Murphy, K., Vunjak-Novakovic, G. and Forgacs, G. Tissue engineering by self-assembly and bioprinting of living cells. *Biofabrication* 2(2): p. 022001, 2010.

Dean, D.M., Napolitano, A.P., Youssef, J., Morgan, J.R. Rods, Tori and Honeycombs. The Directed Self-Assembly of Microtissues with Prescribed Microscale Geometries. *FASEB J.* 21: 4005-4012, 2007.

Napolitano, A.P., Chai, P., Dean, D.M., Morgan, J.R. Dynamics of the Self-Assembly of Complex Cellular Aggregates on Micro-Molded Non-Adhesive Hydrogels. *Tissue Eng.* 13: 2087-2094, 2007.

Napolitano, A.P., Dean, D.M., Man, A.J., Youssef, J., Ho D.N., Rago, A.P, Lech, M.P., Morgan, J.R. Scaffold-free 3-Dimensional Cell Culture Utilizing Micro-Molded Non-Adhesive Hydrogels. *BioTechniques* 43: 494-500, 2007.

Dean, D.M. and Morgan, J.R. Cytoskeletal-Mediated Tension Modulates the Directed Self-assembly of Microtissues. *Tissue Eng.* 14: 1989-1997, 2008.

Rago, A.P., Chai, P., Morgan, J.R. Encapsulated Arrays of Self-Assembled Micro-tissues: An Alternative to Spherical Microcapsules. *Tissue Eng.* 15: 387-395, 2009.

Achilli, T-M., McCalla, S., Tripathi, A. and Morgan, J.R. Quantification of the Kinetics and Extent of Self-sorting in Three Dimensional Spheroids. *Tissue Eng.* 18: 302-309, 2012.

Dean, D.M. and Morgan, J.R. Fibroblast Elongation and Dendritic Extensions in Constrained Versus Unconstrained Microtissues. *Cell Motility and the Cytoskeleton* 66: 129-141, 2009.

Krotz, S.F., Robbins, J.C., Ferruccio, T-M., Moore, R., Steinhoff, M.M., Morgan, J.R. and Carson, S. In Vitro Maturation of Oocytes via Pre-fabricated Self-asssembled Artificial Human Ovary. *J. of Assisted Reproduction and Genetics.* 27: 743-750, 2010.

Robins, J.C., Morgan, J.R., Krueger, P. Carson, S.A. Bioengineering Anembryonic Human Trophoblast Vesicles. *Reproductive Sciences* 18: 128-135, 2011.

Bao, B., Jiang, J. Yanase, T., Nishi, Y., and Morgan, J.R. Connexon-mediated Cell Adhesion Drives Microtissue Self-assembly. *FASEB J.* 25: 255-264, 2011.

Ho, D.N., Kohler, N., Sigdel, A., Killuri, R., Morgan, J.R., Xu, C., Sun, S.S. Penetration of Endothelial Cell Coated Multicellular Tumor Spheroids by Iron Oxide Nanoparticles. *Theranostics.* 2: 66-75, 2012.

Bao, B.A., Lai, C.P.K., Naus, C.C., and Morgan, J.R. Pannexin 1 Drives Multicellular Compaction Via a Signaling Cascade that Upregulates Cytoskeletal Function. *J. Biol Chem.* 287: 8407-8416, 2012.

Desroches, B.R., Zhang, P., Choi, B., Maldonado, A.E., Rago, A., Liu, G.X. Nath, N., King, M.E., Hartmann, K.M., Yang, B., Koren, G., Morgan, J.R. and Mende U. Functional Scaffold-free Cardiac Microtissues: A Novel Model for the Investigation of Heart Cells. *Am J Physiol.*, (2012).

Kelm, J. M., and Fussenegger, M. Microscale tissue engineering using gravity-enforced cell assembly. *Trends in Biotechnology* 22: 195-202, 2004.

Lin R Z and Chang H Y. Recent advances in three-dimensional multicellular spheroid culture for biomedical research *Biotechnol. J.* 3 1172-84, 2008.

Hirschhaeuser, F., Menne, H., Dittfeld, C., West, J., Mueller-Klieser, W., and Kunz-Schughart, L. A. Multicellular tumor spheroids: an underestimated tool is catching up again. *Journal of Biotechnology* 148, 3-15, 2010.

Jong Bin Kim, Three-dimensional tissue culture models in cancer biology, *Seminars in Cancer Biology* 15, 365-377, 2005.

Kunz-Schughart, L. A., Schroeder, J. A., Wondrak, M., van Rey, F., Lehle, K., Hofstaedter F., and Wheatley, D. N. Potential of fibroblasts to regulate the formation of three-dimensional vessel-like structures from endothelial cells in vitro. *Am J Physiol Cell Physiol*, 290, 1385-1398, 2006.

Rouwkema, J., de Boer, J., and Van Blitterswijk, C. A. Endothelial cells assemble into a 3-dimensional prevascular network in a bone tissue engineering construct. *Tissue Eng* 12: 2685-2693, 2006.

Kelm JM, Djonov V, Ittner LM, Fluri D, Born W, Hoerstrup SP, Fussenegger M. Design of custom-shaped vascularized tissue using microtissue spheroids as minimal building units. *Tissue Eng.* 12: 2151-2159, 2006.

Kelm, J.M., Ittner, L.M., Born, W., Djonov, V., Fussenegger, M. Self-assembly of sensory neurons into ganglia-like microtissues. J Biotechnol. 121(1): 86-101, 2006.

Youssef, J., Nurse, A., Freund, L.B. and Morgan, J.R. Quantification of the Forces Driving Self-assembly of 3D Micro-tissues. *Proc. Nat'l. Acad. Sci. USA.* 108: 6993-6998, 2011.

Youssef, J., Chen, P., Shenoy, V.B. and Morgan, J.R. Mechano-Transduction is Enhanced by the Synergistic Action of Heterotypic Cell Interactions and TGF-β1. *FASEB J.* 26: 2522-2530, 2012.

Rago, A.P., Dean, D.M., Morgan, J.R. Controlling Cell Position in Complex Heterotypic 3D Microtissues by Tissue Fusion. *Biotech. & Bioeng.* 102: 1231-1241, 2009.

Truskey, G.A., Yuan, F. and Katz, D. Transport Phenomena in Biological Systems 2nd edition, Pearson Prentice Hall publishers, New York, 2009.

Colton, C.K., Implantable biohybrid artificial organs. *Cell Transplant.* 4: 415-36, 1995.

(56) References Cited

OTHER PUBLICATIONS

Carmeliet, P. and R.K. Jain, Angiogenesis in cancer and other diseases. *Nature* 407, 249-57, 2000.
Ko, H.C., B.K. Milthorpe, and C.D. McFarland, Engineering thick tissues—the vascularisation problem. *Eur Cell Mater.* 14:1-18, 2007.
Morgan J.R., Barrandon Y., Green H., Mulligan R.C. Transfer and expression of foreign genes in transplantable human epidermal cells. *Science* 237:1476-1479, 1987.
Erdag, G., Medalie, D.A., Rakhorst, H., Krueger, G.G., and Morgan, J.R. FGF-7 expression enhances the performance of bioengineered skin. *Molecular Therapy* 10, 76-85, 2004.
Meyer, E.P., Beer, G.M., Lang, A., Manestar, M., Krucker, T., Meier, S., Mihac-Probst, D., Groscurth, P. Polyurethane elastomer: A new materials for the visualization of cadaveric blood vessels. *Clinical Anatomy* 20, 2-7, 2007.
Holt, B., Tripathi, A. and Morgan, J.R. Viscoelastic Response of Human Skin to Low Magnitude Physiologically Relevant Shear. *J. Biomechanics* 41: 2689-2695, 2008.
Holt, B., Tripathi, A. and Morgan, J.R. Designing Poly HEMA Substrates that Mimic the Viscoelastic Response of Soft Tissue. *J. Biomechanics* 44: 1491-1508, 2011.
Guevorkian, K., M.J. Colbert, M. Durth, S. Dufour, and F. Brochard-Wyart, Aspiration of Biological Viscoelastic Drops, Physical Review Letters, 2010. 104(21).
Kunstar, A., et al., "Raman Microspectroscopy : A Non-Invasive Analysis Tool for Monitoring of Collagen-Containing Extracellular Matrix Formation in a Medium-Throughput Culture System," *Tissue Eng. Part C Methods* 17: 737 (2011).
Gwyther, T.A., et al., "Engineered Vascular Tissue Fabricated From Aggregated Smooth Muscle Cells," *Cells Tissues Organs*, 194: 13 (2011).
Birenboim, R., et al., "Simple Generation of Neurons From Human Embryonic Stem Cells Using Agarose Multiwell Dishes," *J. Neurosci. Methods*, 214: 9 (2013).
Boutin, M.E., "Application and Assessment of Optical Clearing Methods for Imaging of Tissue-Engineered Neural Stem Cell Spheres," *Tissue Eng. Part C. Methods*, 2014 [Epub ahead of print]; DOI: 10.1089/ten.tec.2014.0296.
Griffith, L. G. & Naughton, G. Tissue engineering—current challenges and expanding opportunities. *Science* 295, 1009-14 (2002).
Uygun, B. E. et al. Organ reengineering through development of a transplantable recellularized liver graft using decellularized liver matrix. *Nat. Med.* 16, 814-20 (2010).
Hoque, M. E., Mao, H. Q. & Ramakrishna, S. Hybrid braided 3-D scaffold for bioartificial liver assist devices. *J. Biomater. Sci. Polym. Ed.* 18, 45-58 (2007).
Blakely, A. M. et al. in *Biofabrication* (Forgacs, G. & Sun, W.) 149-166 (Elsevier Inc., 2013).
L'Heureux, N. et al. Technology insight: the evolution of tissue-engineered vascular grafts—from research to clinical practice. *Nat. Clin. Pract. Cardiovasc. Med.* 4, 389-95 (2007).
Waymack, P., Duff, R. G. & Sabolinski, M. The effect of a tissue engineered bilayered living skin analog, over meshed split-thickness autografts on the healing of excised burn wounds. The Apligraf Burn Study Group. *Burns* 26, 609-19 (2000).
L'Heureux, N. et al. Human tissue-engineered blood vessels for adult arterial revascularization. *Nat. Med.* 12, 361-5 (2006).
L'Heureux, N., McAllister, T. N. & de la Fuente, L. M. Tissue-engineered blood vessel for adult arterial revascularization. *N. Engl. J. Med.* 357, 1451-3 (2007).
Gonfiotti, A. et al. The first tissue-engineered airway transplantation: 5-year follow-up results. *Lancet* 383, 238-44 (2014).
Priya, S. G., Jungvid, H. & Kumar, A. Skin tissue engineering for tissue repair and regeneration. *Tissue Eng. Part B. Rev.* 14, 105-18 (2008).

Atala, A., Bauer, S. B., Soker, S., Yoo, J. J. & Retik, A. B. Tissue-engineered autologous bladders for patients needing cystoplasty. *Lancet* 367, 1241-6 (2006).
Badylak, S. F., Taylor, D. & Uygun, K. Whole-organ tissue engineering: decellularization and recellularization of three-dimensional matrix scaffolds. *Annu. Rev. Biomed. Eng.* 13, 27-53 (2011).
Younossi, Z. M. et al. Changes in the prevalence of the most common causes of chronic liver diseases in the United States from 1988 to 2008. *Clin. Gastroenterol. Hepatol.* 9, 524-530.e1; quiz e60 (2011).
Leckie, P., Davenport, A. & Jalan, R. Extracorporeal liver support. *Blood Purif.* 34, 158-63 (2012).
Stutchfield, B. M., Simpson, K. & Wigmore, S. J. Systematic review and meta-analysis of survival following extracorporeal liver support. *Br. J. Surg.* 98, 623-31 (2011).
Rouwkema, J., Rivron, N. C. & van Blitterswijk, C. A. Vascularization in tissue engineering. *Trends Biotechnol.* 26, 434-41 (2008).
Wilson, W. C. & Boland, T. Cell and organ printing 1: protein and cell printers. *Anat. Rec. A. Discov. Mol. Cell. Evol. Biol.* 272, 491-6 (2003).
Jakab, K. et al. Tissue engineering by self-assembly and bio-printing of living cells. *Biofabrication* 2, 22001 (2010).
Norotte, C., Marga, F. S., Niklason, L. E. & Forgacs, G. Scaffold-free vascular tissue engineering using bioprinting. *Biomaterials* 30, 5910-7 (2009).
McGuigan, A. P. & Sefton, M. V. Vascularized organoid engineered by modular assembly enables blood perfusion. *Proc. Natl. Acad. Sci. U. S. A.* 103, 11461-6 (2006).
Du, Y., Lo, E., Ali, S. & Khademhosseini, A. Directed assembly of cell-laden microgels for fabrication of 3D tissue constructs. *Proc. Natl. Acad. Sci. U. S. A.* 105, 9522-7 (2008).
Choi, N. W. et al. Microfluidic scaffolds for tissue engineering. *Nat. Mater.* 6, 908-15 (2007).
Cuchiara, M. P., Allen, A. C. B., Chen, T. M., Miller, J. S. & West, J. L. Multilayer microfluidic PEGDA hydrogels. *Biomaterials* 31, 5491-7 (2010).
Golden, A. P. & Tien, J. Fabrication of microfluidic hydrogels using molded gelatin as a sacrificial element. *Lab Chip* 7, 720-5 (2007).
Miller, J. S. et al. Rapid casting of patterned vascular networks for perfusable engineered three-dimensional tissues. *Nat. Mater.* 11, 768-74 (2012).
Bianconi, E. et al. An estimation of the number of cells in the human body. *Ann. Hum. Biol.* 40, 463-71, (2013).
Heinemann, A., Wischhusen, F., Püschel, K. & Rogiers, X. Standard liver volume in the Caucasian population. *Liver Transpl. Surg.* 5, 366-8 (1999).
Svoronos, A. A., Tejavibulya, N., Schell, J. Y., Shenoy, V. B. & Morgan, J. R. Micro-mold design controls the 3D morphological evolution of self-assembling multicellular microtissues. *Tissue Eng. Part A* 20, 1134-44 (2014).
LeHong, H., et al., "Key Trends to Watch in Gartner 2012 Emerging Technologies Hype Cycle," www.forbes.com/sites/gartnergroup/2012/09/18/key-trends-to-watch-in-gartner-2012.
Robinson, M.A., "Medical Miracle: Biotech Duo is "Printing" New Organs," www.money.morning.com/2013/03/01/medical-miracle-biotech-duo-is-printing-new-organs/; (2103).
Fitzwater, R., "Organovo's 3D Bioprinting: A Win for Pharmaceuticals?" www.investmentu.com/article/detail/28026/organovo-3d-bioprinting-pharmaceuticals (2012).
Hotz, R.L., "Printing Evolves: An Inkjet for Living Tissue," The Wall Street Journal, Sep. 18, 2012.
Basenese, L., "Two Fast-Growing Trends That Are Ripe For Investing Right Now," Archive TI, 3-D Printing, Biotechnology, Healthcare & Big Pharma (2013).
Mero, D., "A Way to Invest in Biotech and 3D Printing, All at Once," www.seekingalpha.com/article/890721-a-way-to-invest-in-biotech-and-3d-printing-all-at-once (2012).

* cited by examiner

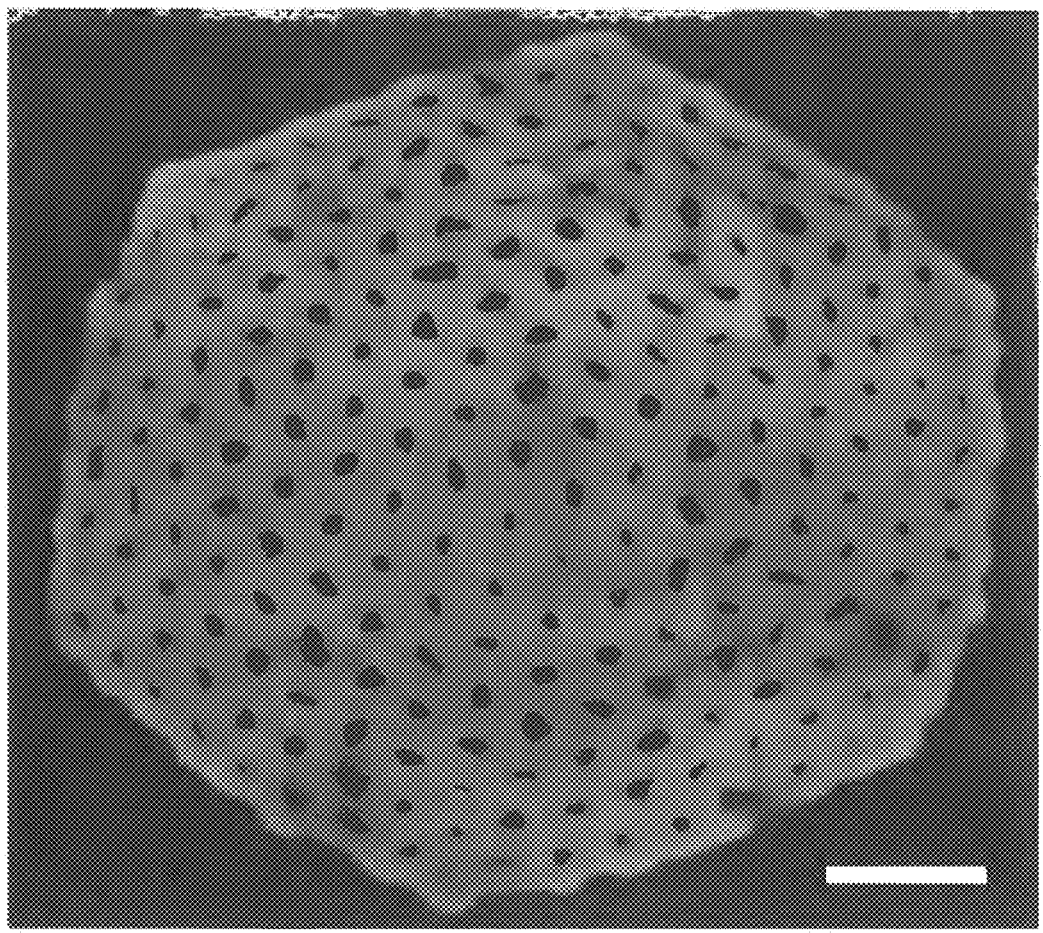
(PRIOR ART)
FIG. 1
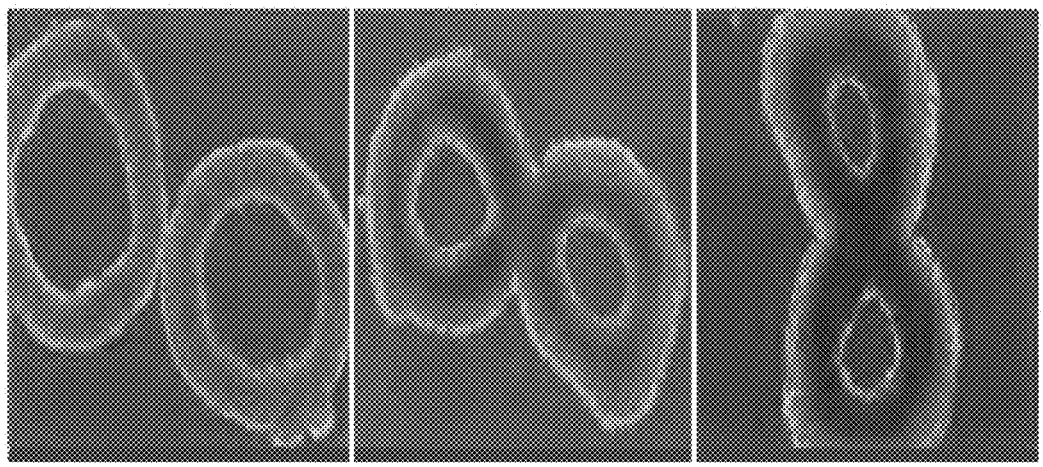
(PRIOR ART)
FIG. 2A
(PRIOR ART)
FIG. 2B
(PRIOR ART)
FIG. 2C

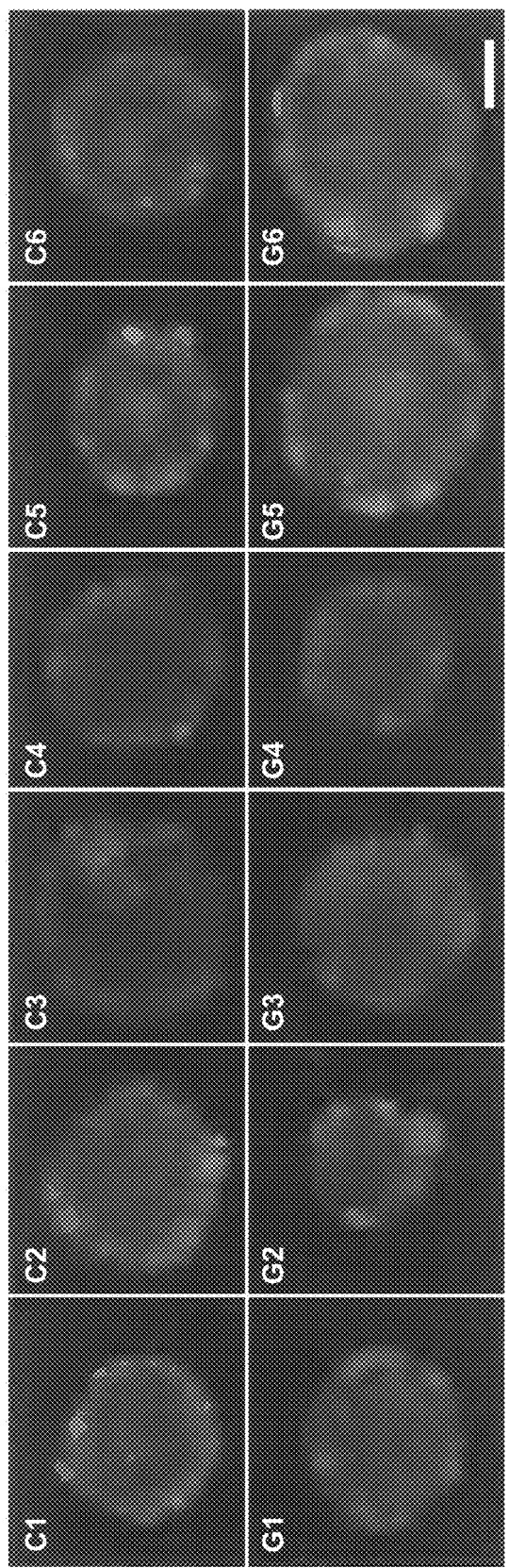

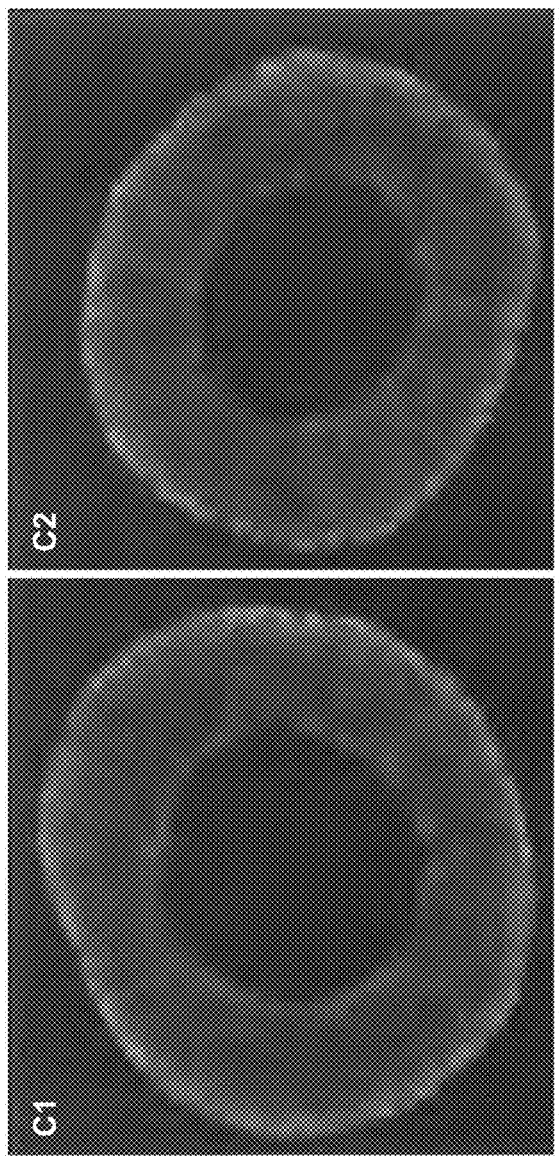
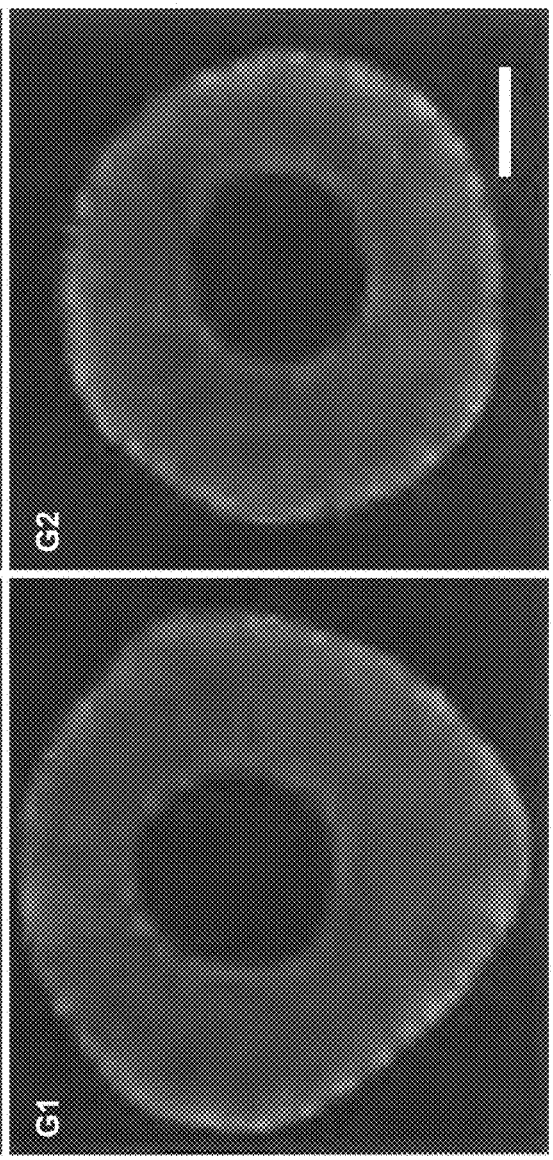
FIG. 25A FIG. 25B FIG. 25C FIG. 25D

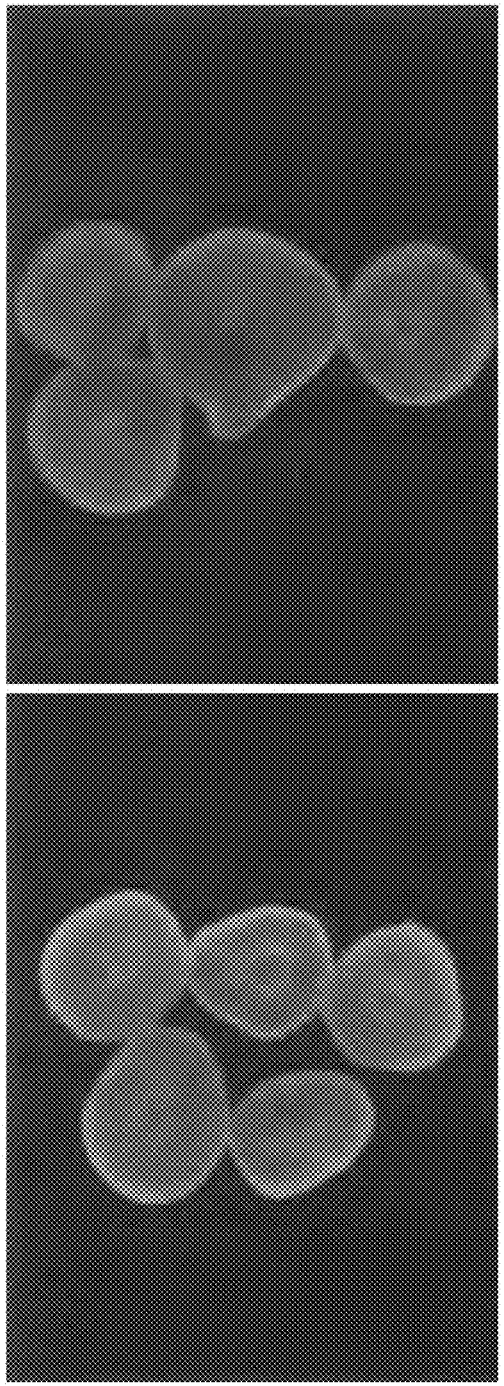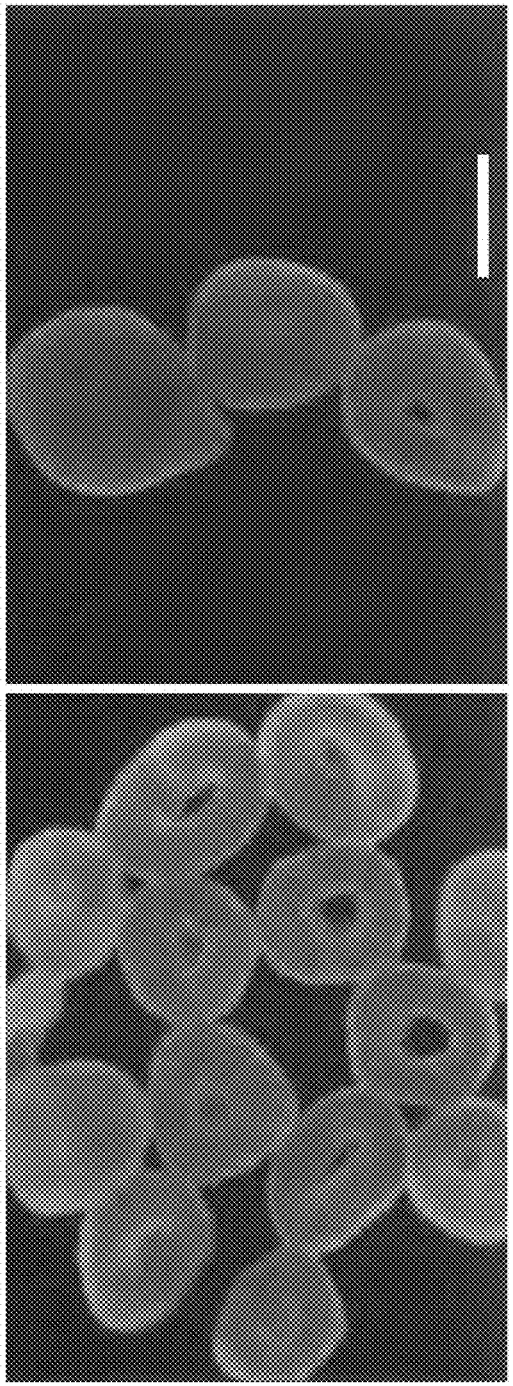

DEVICE AND METHOD FOR ENGINEERING LIVING TISSUES

RELATED APPLICATION

This application claims the benefit of U.S. Provisional Application No. 61/846,703, filed on Jul. 16, 2013.

The entire teachings of the above application is incorporated herein by reference.

GOVERNMENT SUPPORT

This invention was made with government support under the National Institutes of Health T32 Trauma Grant, number 5T32GM065085-09. The government has certain rights in the invention.

BACKGROUND OF THE INVENTION

First reported in 2005, bio-printers (adapted inkjet printers) were developed to try and meet the challenge of printing 3D organs, but they have had very limited success (3-17). They fabricate structures via a dropwise printing of cells with an extracellular matrix (ECM) material, which serves as the "bio-glue". The bio-glue gels within minutes, but the cells require tens of hours to attach to the ECM. Recently, bio-printers have become commercially available (Envisio-Tec, Organovo, Inc). However, success is limited to simple structures such as a single tube or an array of spheroids (17). The structures survive by passive diffusion and none even begin to approach the complexity, nor cell density of an organ. Bio-printers are also limited by slow throughput inherent in the small size/simplicity of their building materials as well as the vast number of building units that must be deposited. Bio-printers deposit (one at a time) a drop of either a spheroid (~1,000 cells) or liquid ECM. Our single honeycomb building part has $6\times10^6$ cells, equivalent to 6,000 spheroids. Bio-printers are not creating thick structures with sufficient density of cells to require perfusion. They are creating structures of modest thickness, high ECM content and low cell density that do not require perfusion.

Current pick-and-place instruments from the electronics industry are not suitable, nor could they be easily modified since our building must always occur within an aqueous environment of cell culture medium. We also investigated microbiology instruments for picking bacterial colonies and these were deemed not suitable because they locate a colony and punch out a small plug of agarose and dispense this plug (with colony) to a 96 well plate. These instruments (e.g., Hudson Robotics) are designed for very high throughput, do not have the precision we need, would certainly damage our tissues and cannot grip, let alone perfuse a growing organ. Hence, there is no off the shelf pick and place device available which we can modify for our intended research projects.

Therefore, a new device and method are that overcome or minimize the above-referenced problems.

SUMMARY OF THE INVENTION

The invention generally is directed to a device and method for assembling aggregations of adherent cells.

In one embodiment, the invention is a device for assembling aggregations of adherent cells that includes an assembly vessel. A gripper is movable within the assembly vessel. The gripper includes a gripper housing defining a gripper chamber and at least two openings, a gripper membrane over one of the openings, a conduit extending from another of the openings of the gripper, and a support at the gripper housing that controls the position of the gripper within the housing. A perfusate source is in fluid communication with the conduit extending from the gripper housing. A build support is fixed within the assembly vessel that includes a build housing defining a build chamber and at least two openings, a support membrane over one of the openings, and a conduit extending from another of the openings of the build support to the perfusate source.

In another embodiment of the invention, a method of assembling aggregations of adherent cells includes the step of securing a first aggregation of cells to a gripping membrane by directing a perfusate through the gripping membrane. The gripping membrane is moved to a build membrane opposing the gripping membrane, and the first aggregation of cells is transferred from the gripping membrane to the build membrane by directing perfusate across the first aggregation of cells in a direction toward the build membrane and then through to build membrane. A second aggregation of cells is secured to the gripping membrane by directing perfusate through the gripping membrane. The gripping membrane is moved to the first aggregation of cells at the build membrane, and the second aggregation of cells is transferred from the gripping membrane to the first aggregation of cells by directing perfusate across the second aggregation of cells and the first aggregation of cells and then through the build membrane, whereby the first and second aggregations of cells are stacked on the build membrane, thereby assembling the aggregation of cells.

The device and method described herein are in the field of tissue engineering, namely the in vitro engineering of thick tissues of high cell density. "Thick tissue," as that term is defined herein, means tissues that are greater in thickness than 200 microns.

"High cell density," as that term is defined herein, means at least about $10^8$ cells/ml. An example of tissue having "high cell density" is the human liver. The number of cells in the human liver is estimated to be ~240 billion (Bianconi et al. An Estimation of the Number of Cells in the Human Body. *Annals of Human Biology,* 40, 463-471, 2013). The volume of the liver, which needs to be estimated for purposes of partial hepatectomy, is ~2 liters (Heinemann et al., Standard Liver Volume in the Caucasian Population. *Liver Transplantation and Surgery* 5: 366-368, 1999). Thus, cell density in a real liver is $10^8$ cells/ml.

The device of the invention does not rely on bio-inks that might be toxic and need to be washed out of a construct. Also the device of the invention can employ large living parts that have very high cell density. The living parts are formed by cells aggregating with each other (cell-driven self-assembly).

The invention, however, is not limited to thick tissue and high cell density; it can be employed to pick, place and perfuse materials that are not "thick" or of "high cell density."

It assembles relatively large 3D tissues/organs layer-by-layer using a controllable low level suction head to pick up living microtissue building parts and place them onto other microtissue building parts in precise locations, while maintaining perfusion as these parts fuse and the living structure is built. This is a versatile building platform that can grip multi-cellular building parts of any size, shape and cell type. Large living building parts in the shape of a honeycomb and, when stacked, the aligned lumens of these honeycomb parts will form channels that enable perfusion of the organ under construction. Success at breaking this "sound barrier" and the ability to build organs in vitro has a far-reaching impact in the field of tissue engineering as well as many other areas of research that use animals. Many of these programs have an unmet need to create new more complex 3D in vitro models (test beds) that more accurately mimic the complexity of in vivo. In addition to reducing the use of animals in research, these models are less expensive and more amenable to investigation. The device and method of the invention can be employed to construct complex 3D test beds of tissues of specified shape and size to study these cellular and molecular events; and to understand the transport of drugs and small molecules.

Investigating and modeling the 3D transport of drugs into tissues, the effects of drugs known to inhibit efflux pumps such as Pgp (P-glycoprotein is an efflux drug transporter), that move small molecules and drugs out of cells, quantitative 3D model and algorithm will facilitate discovering new, more effective inhibitors of drug efflux transporters, 2D cell culture does not adequately mimic drug transport in vivo, which is, more often than not, through multiple layers of different cells. The device also constructs complex 3D test beds of different cell types, layering of cells and composite microtissues of different cell types (normal & pathologic) into desired shapes.

The device assembles/engineers large 3D tissues/organs layer-by-layer using a controllable, low-level fluid suction head to pick up living building parts and place them onto other building parts in precise locations while maintaining perfusion as this living structure is built. This is a versatile building platform that can grip multi-cellular building parts (of any size and shape), image the part it has gripped and then precisely place this part onto a stack of living building parts to effect the layer-by-layer engineering of a solid organ. Each living part has carefully designed lumen structures and is composed of tens of millions of cells formed in specific geometries designed to be stacked and used to build a large 3D tissue/organ complete with a branched tubular (vascular) network for perfusion. Each living part can be designed to have lumens of different sizes and when these building parts are stacked, their lumens can align to form a branching tubular network that can be perfused. An example of a suitable prior art building part is a large honeycomb structure (FIG. 1), as described in Tejavibulya, N., et al., Directed Self-Assembly of Large Scaffold-Free Multi-Cellular Honeycomb Structures, *Biofabrication* 3, 1-9, 2011. The honeycomb-shaped building part can be made by seeding mono-dispersed cells into specially designed non-adhesive agarose micro-molds. Within twenty-four hours, the cells in this scaffold-free environment aggregated and self-assembled a multi-cellular structure in the shape of the honeycomb. The contiguous multi-cellular honeycomb formed around agarose posts which directed the formation of lumens in the honeycomb. This tissue sheet is 2 cm end-to-end in the x, y dimensions and less than 200 μm in the z dimension. Thus, each cell in the honeycomb receives adequate oxygen and nutrients because it is no more than 100 μm away from the top surface, bottom surface or the surface of a nearby lumen. Using CAD and rapid prototyping, micro-molded hydrogels of virtually any size and shape can be designed and these micro-molds direct self-assembly of living cells into the final shape of the building part. This process works for over fifty different cell types including primary human cells from a variety of tissues and organs. And further, these living building parts will readily fuse with one another to form even larger prior art living structures, as described, for example, in Livotti and Morgan Tissue engineering Livotti, C. M., and Morgan, J. R. Self-Assembly and Tissue Fusion of Toroid-Shaped Minimal Building Units. *Tissue Eng.* 16: 2051-2061, 2010 (PMCID: PMC2949232).

Shown in FIG. 2, are two prior art toroid-shaped parts of liver cells that have fused within two days published in Livotti and Morgan. Fusion does not occur between building parts made using conventional tissue engineering approaches where cells are seeded onto a scaffold. Because the parts are made entirely of cells with no added scaffold, they fuse with each other via the same cell-to-cell contacts that drove the self-assembly of the original part from millions of individual cells. Thus, we have a process that can potentially make an indefinite number of building parts of any design in two days, and these parts can be fused within four days to form a larger structure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1 is a photograph of one embodiment of a prior art aggregation of cells configured as a honeycomb, and suitable as a viable building unit by the device and method of the invention. The honeycomb included about $6 \times 10^6$ cells formed in a micro-mold and stained for viability after 24 hrs. Viable cells are green. Dead cells are red. Shown is the merged red and green fluorescent stitched image. Bar 1800 μm. (1).

FIG. 2 are photographs of Toroids (about 20,000 cells each) suitable for use in the present invention and undergoing fusion in all dimensions. Two prior art self-assembled toroids placed adjacent on flat nonadhesive agarose fused in the x-y (horizontal) plane. Images at days 0, 2, 4 (FIGS. 2A-2C). Bars 200 μm.

FIG. 23 is a series of photographs of live/dead staining of control (FIGS. 23A-23C) and gripped (FIGS. 23D-23F) H35 spheroids. Scale bar 100 microns.

FIGS. 25A-25D are photographs of live/dead staining of ungripped control (FIGS. 25A, 25B) and gripped (FIGS. 25C, 25D) KGN toroids, 30,000 cells/toroid. Scale bar 200 microns.

FIGS. 26A-26D are photographs of live/dead staining of gripped KGN toroids after fusion; FIGS. 26A, 26B 30,000 cells/toroid, FIGS. 26C, 26D 40,000 cells/toroid. Scale bar 500 microns.

DETAILED DESCRIPTION OF THE INVENTION

The invention generally is directed to a device and method for assembly aggregation of adherent cells. The invention is also directed to three-dimensional assemblies adherent cells.

FIG. 1 (Prior art) is one embodiment of aggregations of adherent cells according to the method of the invention, employing a device of the invention. Specifically, shown in FIG. 1 is an orbital honeycomb of about six times ten to the sixth cells formed in a micro-mold and stained for viability after 24 hours. The viable cells are shown in green. Dead cells are shown in red. The image shown is the emerged red and green fluorescent stitched image.

In another embodiment, shown in FIG. 2 (Prior art), the aggregation of inherent cells is in the form of a toroid, as shown in FIG. 2, of about 20,000 cells each, which undergo fusion in all directions. FIG. 2 is an image of two self-assembled toroids placed adjacent on flat non-adhesive agarose fused in a plane. The images are shown at days 0, 2, 4 (FIGS. 2A through 2C).

Aggregations of cells, such as are shown in FIGS. 1 and 2, that are suitable for use in by the device and in the method of the invention, can be formed by a method known in the art, such as is described, for example, in U.S. Pat. No.

8,361,781 B2, issued Jan. 29, 2013, by Morgan et al., the entire teachings of which are incorporated herein by reference.

Examples of suitable cells for use by the device and the method of the invention include many different cell types including but not limited to primary cells including hepatocytes, cardiomyocytes, kidney cells, pancreatic cells, fibroblasts, myocytes, epithelial cells, corneal epithelial cells, stromal cells, stem cells, induced pluripotent stem cells, smooth muscle cells, muscle cells, chondrocytes, neural cells, ligament cells, tendon cells, ovarian cells, thyroid cells, parathyroid cells, and also many different kinds of cell lines including but not limited to MCF-7 cells, KGN cells, HEK cells, 3T3 fibroblasts, HepG2 cells, HepG2C3A cells, H35 cells.

Figure 3:
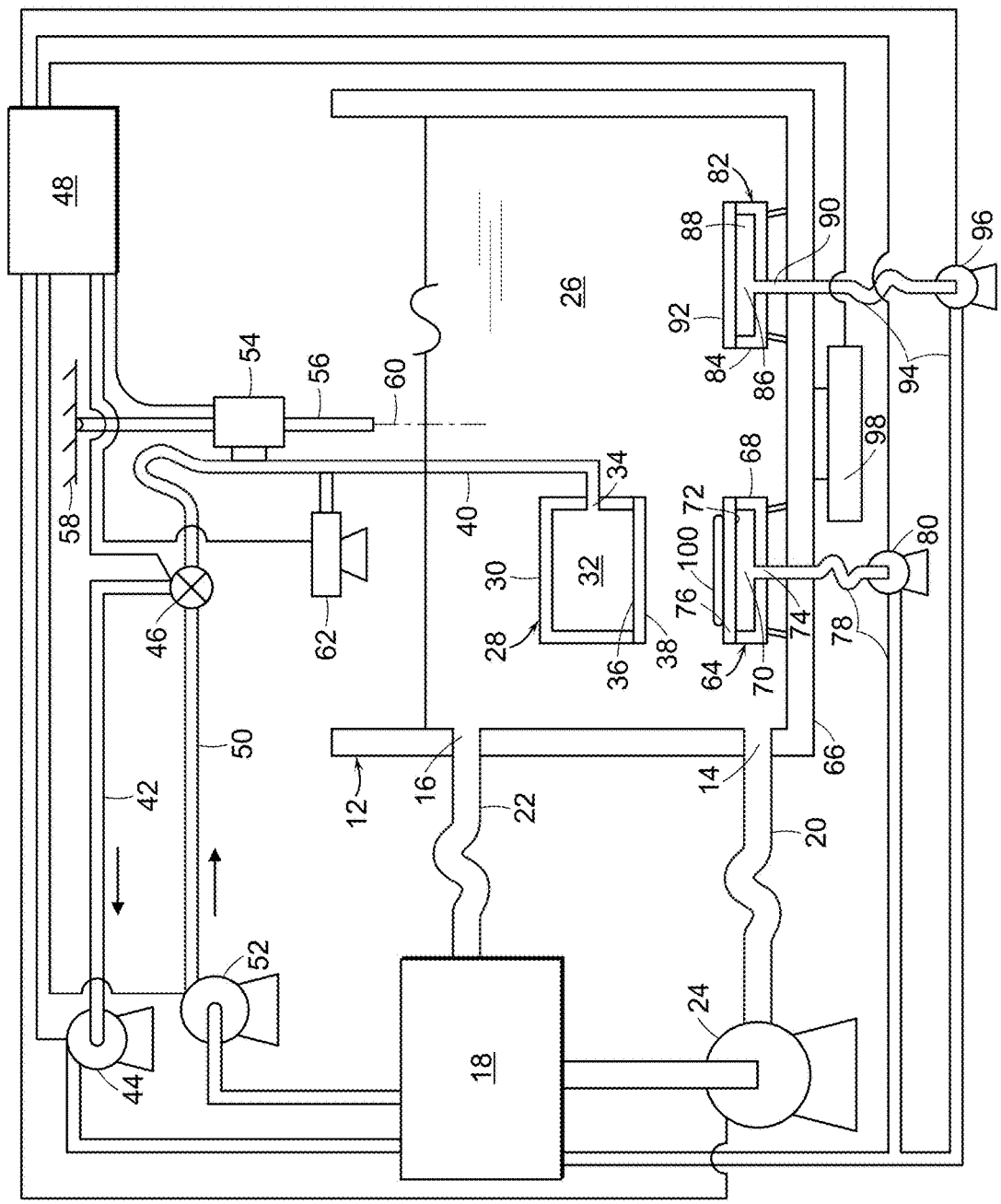
FIG. 3 is a schematic representation of one embodiment of a device of the invention, wherein an aggregation of cells is supported by a staging support.

One embodiment of a device of the invention for assembling aggregations of adherent cells is shown in schematic form in FIG. 3. As shown therein, FIG. 3 includes device 10 of the invention for assembling aggregations of adherent cells. Device 10 includes assembly vessel 12 defining inlet 14 and outlet 16. A suitable material of construction of assembly vessel can include, for example, plexiglass. In one embodiment, assembly vessel 12 is formed of plexiglass. In a specific embodiment, assembly vessel 12 is transparent. Assembly vessel 12 is in fluid communication with perfusate source 18 at inlet 14 and outlet 16 through conduits 20, 22, respectively. Perfusate pump 24 at conduit 20 is employed to control the rate of recirculation of perfusate 26 through assembly vessel 12 and perfusate source 18. Perfusate source 18 is a suitable source of perfusate to sustain the aggregations of cells within assembly vessel 12, such as is known in the art. Examples of suitable perfusates recirculated through perfusate source include, for example, cell culture medium such as DMEM Dulbecco's Modified Eagles' media, all of which, are well known in the art. In another embodiment, not shown, pumps are employed to recirculate perfusate through components within assembly vessel without use of a separate perfusate source vessel.

Gripper 28 within assembly vessel 12 includes gripper housing 30 defining gripper chamber 32 and at least two openings 34, 36. Suitable materials of construction of gripper housing include, for example, polystyrene and glass. Gripper membrane 38 is affixed over an opening 36, as shown in FIG. 1. Examples of suitable membranes for use as gripper membrane at gripper housing 30 include, Millicell cell culture inserts (EMD Millipore, Billerica, Mass.) (12 mm diameter, 10 mm height), which have a polycarbonate membrane with track-etched 3-micron (gripper) or 8-micron (build) pores. Also those versed in the art will know there are other porous membranes as well as porous structures besides membranes that can be used to grip tissues. In one embodiment, gripper membrane 38 has a pore size diameter of about 3 µm and a pore density of about $2 \times 10^6$ pores/cm$^2$. In another embodiment, the pore size diameter is about 8 µm and a pore density of about $1 \times 10^5$ pores/cm$^2$. Gripper housing 30 is supported by support 40 at gripper housing 30. In the embodiment shown in FIG. 3, support 40 also operates as a conduit extending from opening 34 of gripper housing 30 and provides fluid communication between chamber 32 defined by gripper housing 30 and perfusate source 18 through conduit 42, and pump 44. Optionally, three-way valve 46, which is controlled by controller 48 at the intersection of conduits 40, 42 and 50, is included and provides an option for reversing the flow of perfusate through conduit 40 by terminating flow through conduit 42 and pump 44, and opening fluid communication between perfusate source 18 and gripper 28 through conduit 50 and pump 52. Alternatively, when the pump is a peristaltic pump, or positive displacement pump, manifold and three-way valve are not needed, and flow is reversed at conduit by simply reversing the operation of the pump.

Conduit 40 is fixed to micromanipulator 54 which, in turn, is supported by post 56 mounted to rigid external support 58. Micromanipulator 54 is controlled by controller 48 and, upon actuation by controller 48, rotates about post 56, thereby causing rotation of gripper 28 about major longitudinal axis 60 extending through post 56. Micromanipulator 54, also upon actuation of controller 48, is movable along major longitudinal axis 60 of post 56, thereby raising and lowering gripper 28 within assembly vessel 12. Visualization device 62, such as a microscope at conduit 40 is directed toward gripper 28 and, by virtue of transparency of the material of gripper housing 30 and gripper membrane 38, images aggregations of cells within assembly vessel 28 and below gripper membrane 38. Visualization device 62 is operated by controller 48. Visualization device 62 will move with movement of conduit 40 supporting gripper 28. Alternatively, or optionally, in another embodiment, not shown, at least one visualization device is located at at least one of a transparent bottom or side of assembly vessel 12.

Staging support 64 is fixed within assembly vessel 12 at bottom portion 66 of assembly vessel 28. Staging support 64 includes staging housing 68 defining staging chamber 70 and at least two openings 72, 74. Staging membrane 76 extends over and seals opening 72 of staging housing 68. Staging membrane 76 can be of the same or a different type of material or porosity than the gripper membrane. Conduit 78 extends from other opening 74 of staging housing 68 and through pump 80 to perfusate source 18. The material of construction of staging housing 68 and staging membrane 76 can be the same as that of gripper 28, although they need not be transparent. Optionally, rigid support or mold, not shown, is fixed to staging membrane 76 in order to assist in retaining an aggregation of cells at staging membrane 76.

Build support 82 is fixed within assembly vessel 12, as is staging support 64. Build support 82 includes build housing 84 defining build chamber 86 and at least two openings 88, 90. Build membrane 92 extends over and seals opening 88 of build housing 84. Suitable membranes include those employed as the gripper membrane, such as a membrane having a pore size diameter of about 8 µm and a pore density of about $1 \times 10^5$ pores/cm$^2$. The build membrane can be of the same or different type of material or porosity than the gripper membrane and the staging membrane. Conduit 94 extends from another opening 90 of build housing 84 and extends through pump 96 to perfusate source 18. Optionally, rigid support or mold (not shown) is fixed at build membrane 92 to assist in support of an aggregation of cells at build membrane 92. Preferably, staging membrane 76 and build membrane 92 are in a common plane. Preferably the common plane in which support membrane 76 and build membrane 92 lie is transverse to and, most preferably, normal to the major longitudinal axis 60 of post 56 extending from support 58.

Assembly vessel support 98 is fixed to assembly vessel 12. Assembly vessel support 98 controls movement of assembly vessel 12 in a plane essentially normal to major longitudinal axis 60 of post 56 extending from support 58. The position of assembly vessel 12 by virtue of assembly vessel support 98 is controlled by controller 48.

In one embodiment of the invention, device 10 of the invention represented in FIG. 3 is employed to conduct an embodiment of the method of the invention by moving aggregations of cells resting on one or more staging supports 64 within assembly vessel 12 to build support 82 to thereby obtain a stack of aggregations of adherent cells on build support 82. In one embodiment, the method of the invention includes the following steps.

Aggregation of cells 100 is deposited on staging membrane 76. In one embodiment, assembly vessel 12 contains a plurality of staging supports 64, each of which support at a respective staging membrane 76 at least one aggregation of cells. Aggregations of cells are either deposited at staging membranes or grown at staging membranes by a suitable method, such as is described in U.S. Pat. No. 8,361,781 B2, issued Jan. 29, 2013, by Morgan et al., the entire teachings of which are incorporated herein by reference in their entirety. The rate of perfusate flow across aggregation of cells 100 at staging membrane 76 by direction of perfusate 26 from assembly vessel 12 through staging membrane 76 and into staging support 64 is sufficient to sustain aggregation of cells 100 with nutrients and oxygen. Alternatively, aggregation of cells 100 is not supported by staging support 64, but, rather, is grown in a separate vessel (not shown) and transferred to assembly vessel by a suitable means, wherein they lie essentially randomly at the bottom of assembly vessel 12. In this latter embodiment, visualization device 62 and gripper 28 can be employed to locate and then selectively secure individual aggregations of cells to gripper membrane 38 for transfer to build support 82.

Figure 4:
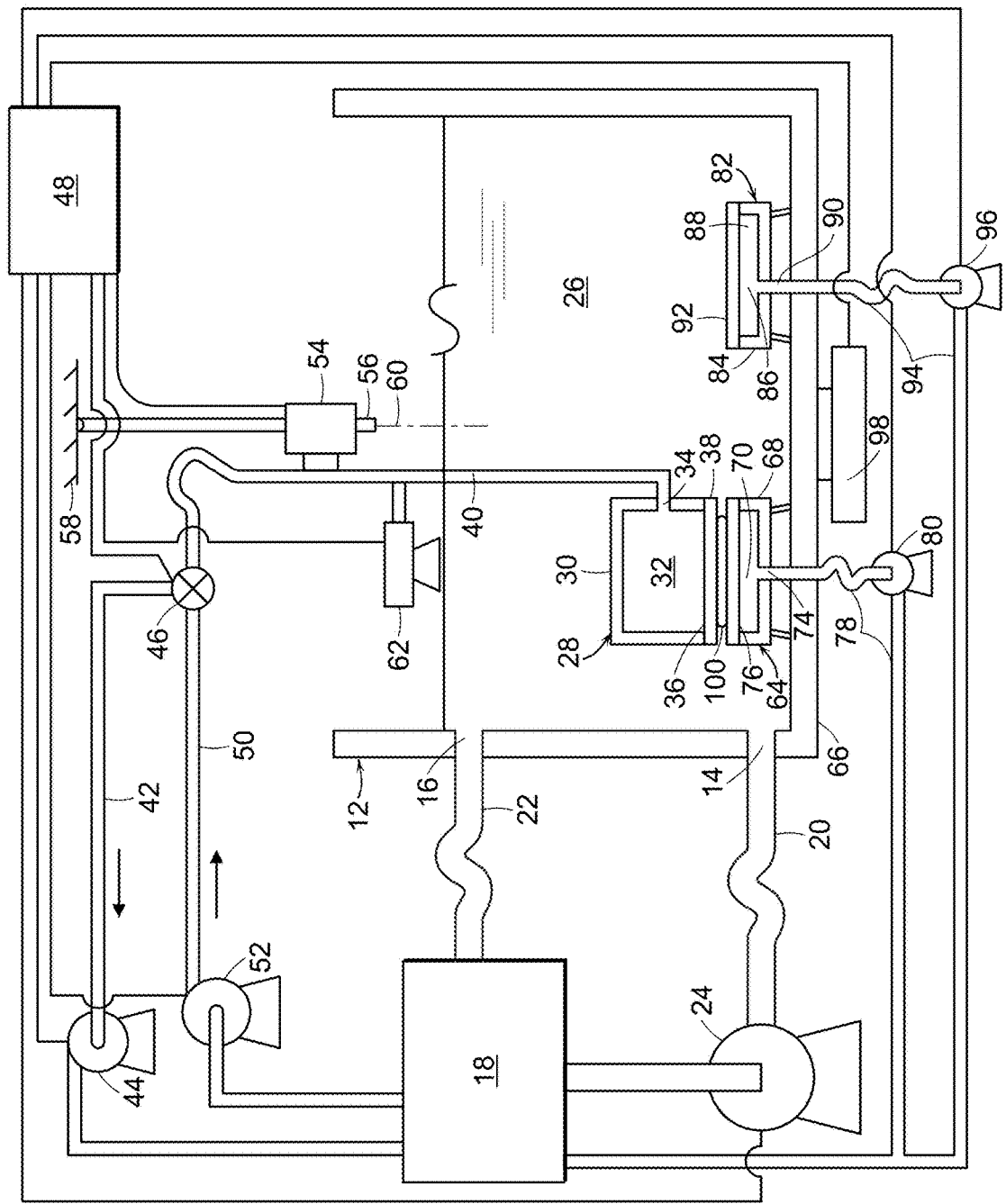
FIG. 4 is the embodiment of the device of FIG. 3, wherein a gripper of the invention has been lowered to the aggregation of cells supported by the staging support.

Returning to the method employed by the apparatus shown in FIG. 3, visualization device 62 is employed to identify aggregation of cells 100 lying on staging membrane 76 within assembly vessel 12 by use of controller 48. Once identified, support 40, including visualization device 62 and gripper 28, are lowered by actuation of micromanipulator 54 to cause movement of micromanipulator 54 along major longitudinal axis 60 of post 56 by controller 48 until gripper membrane 38 is adjacent to aggregation of cells 100 at staging membrane 76, as shown in FIG. 4.

Perfusate 26 is directed from assembly vessel 12 through gripper membrane 38 and conduit 40, 42 by actuation of pump 44, whereby perfusate 26 is directed from gripper housing 30 through conduits 40, 42 and pump 44 to perfusate source 18 causes a direction of flow of perfusate 26 through gripper membrane 38 at a rate and velocity that is greater than that of perfusate 26 directed through staging membrane 76 into staging housing 68 and pump 80 back to perfusate source 18. As a consequence, aggregation of cells 100 will preferentially be directed toward gripper membrane 38. The rate of flow of perfusate 26 is sufficient to sustain the aggregation of cells 100 at gripper membrane 38.

Figure 5:
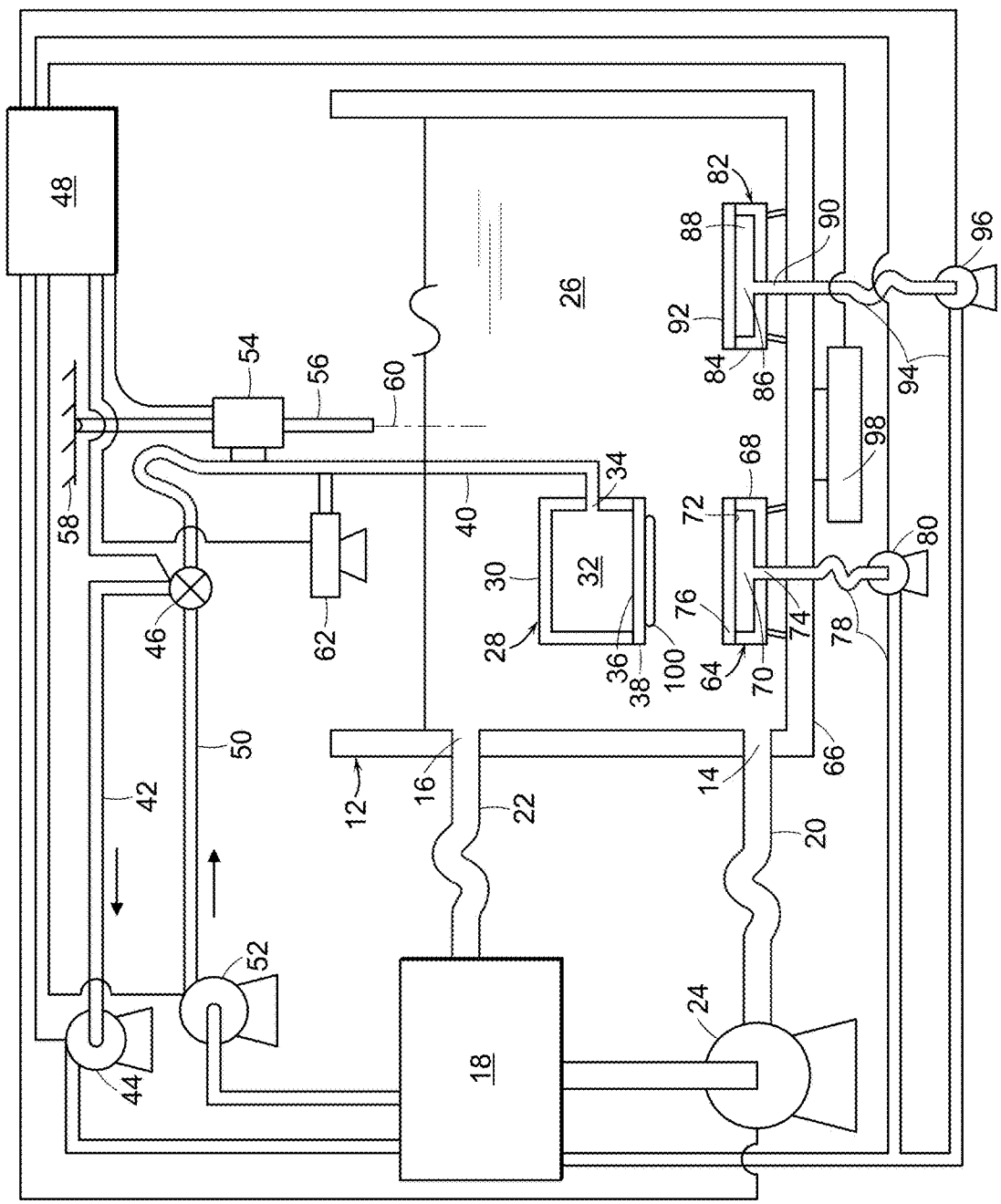
FIG. 5 is the embodiment of the device of FIG. 4, wherein the gripper has been raised from the staging support while gripping the agglomeration of cells.

As shown in FIG. 5, micromanipulator 54 is actuated by controller 48 to thereby cause micromanipulator 56 to move upward along major longitudinal axis 60 of post 56, causing gripper 28, in turn, to move away from staging membrane 76 while aggregation of cells 100 remains at gripper membrane 38, thereby raising aggregation of cells 100 away from staging membrane 76.

Figure 6:
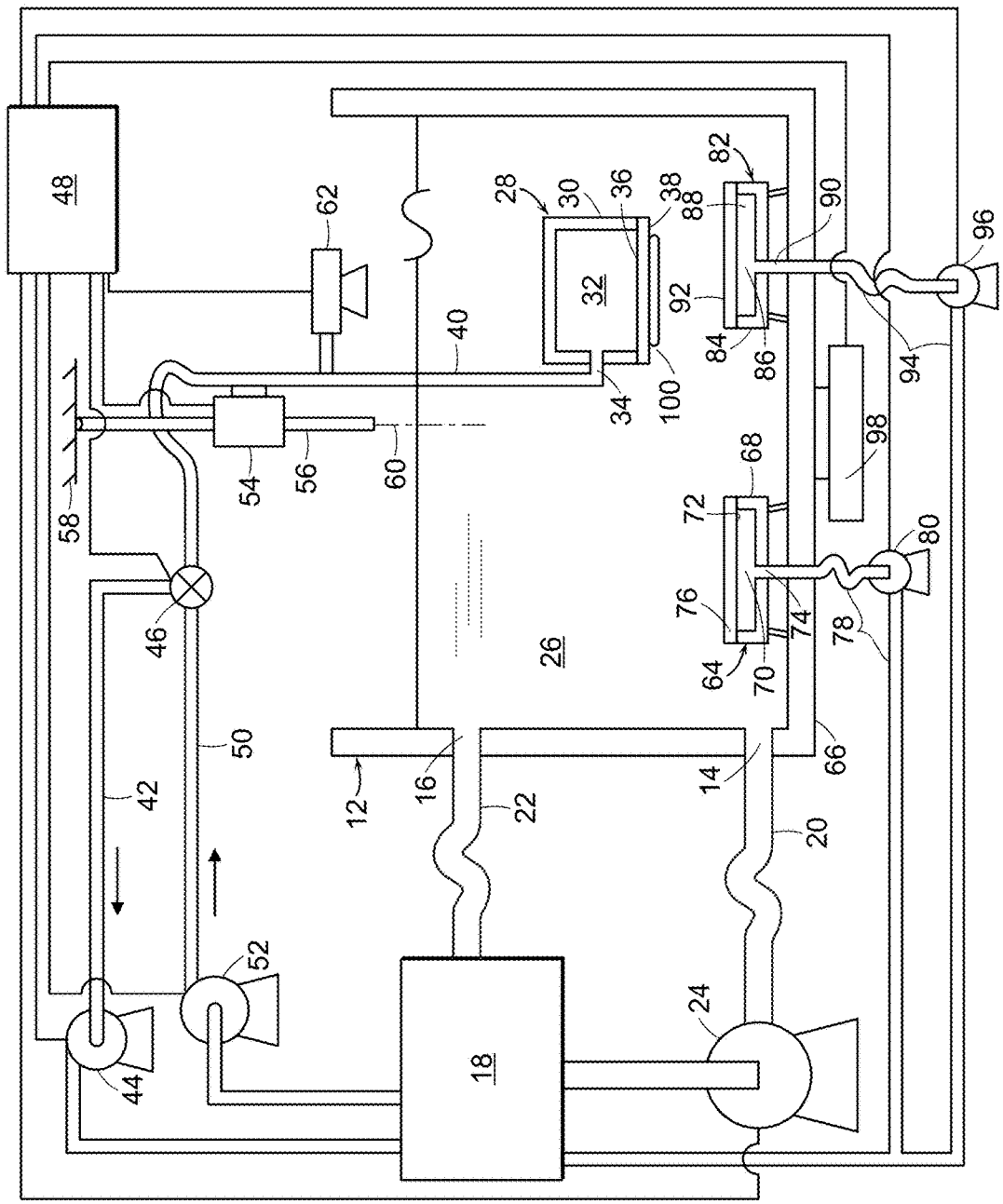
FIG. 6 is the embodiment of the device of FIG. 5, wherein the gripper has been rotated about a vertical axis to thereby bring the aggregation of cells into proximity of a build support of the invention.

As shown in FIG. 6 micromanipulator 54 is then rotated about major longitudinal axis 60 of post 56 by operation of controller 48, thereby also causing gripper 28 and visualization device 62 to rotate about major longitudinal axis 60 of post 56, whereby gripper 28 and aggregation of cells 100 at gripper membrane 38 are brought into relatively close proximity to build support 82.

Figure 7:
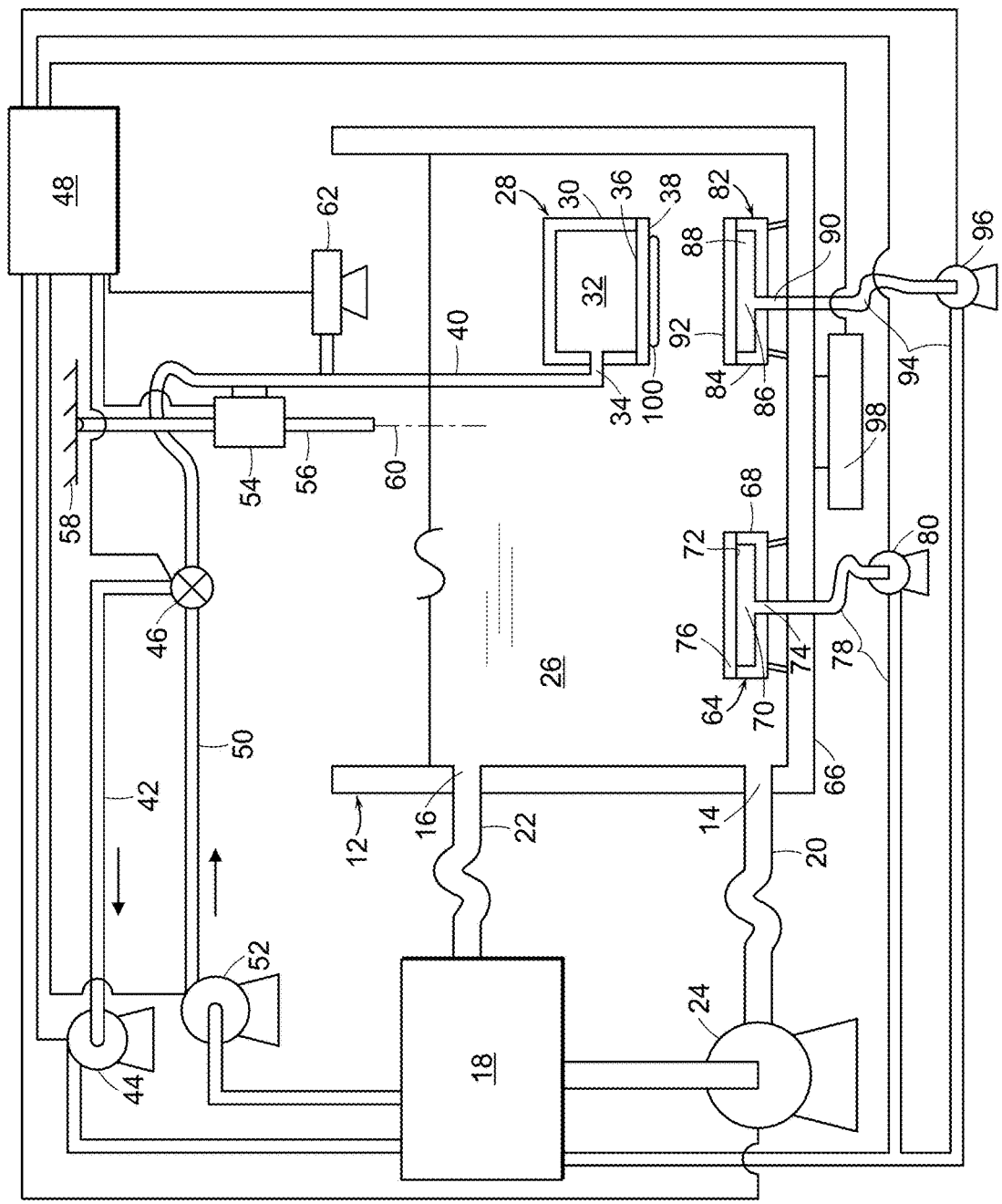
FIG. 7 is the embodiment of the devices of FIG. 6, wherein the gripper has been brought into essentially vertical alignment with the build support by movement of the assembly vessel in a horizontal (x,y) plane.

As shown in FIG. 7, assembly vessel support 98 is actuated by use of visualization device 62 and controller 48 to bring aggregation of cells 100 into alignment with build membrane 92. Assembly vessel support 98, as stated above, operates to move build membrane 92 in a plane that is transverse to and, preferably, normal to major longitudinal axis 60 of post 56 about which gripper 28 rotates by actuation of micromanipulator 56.

Figure 8:
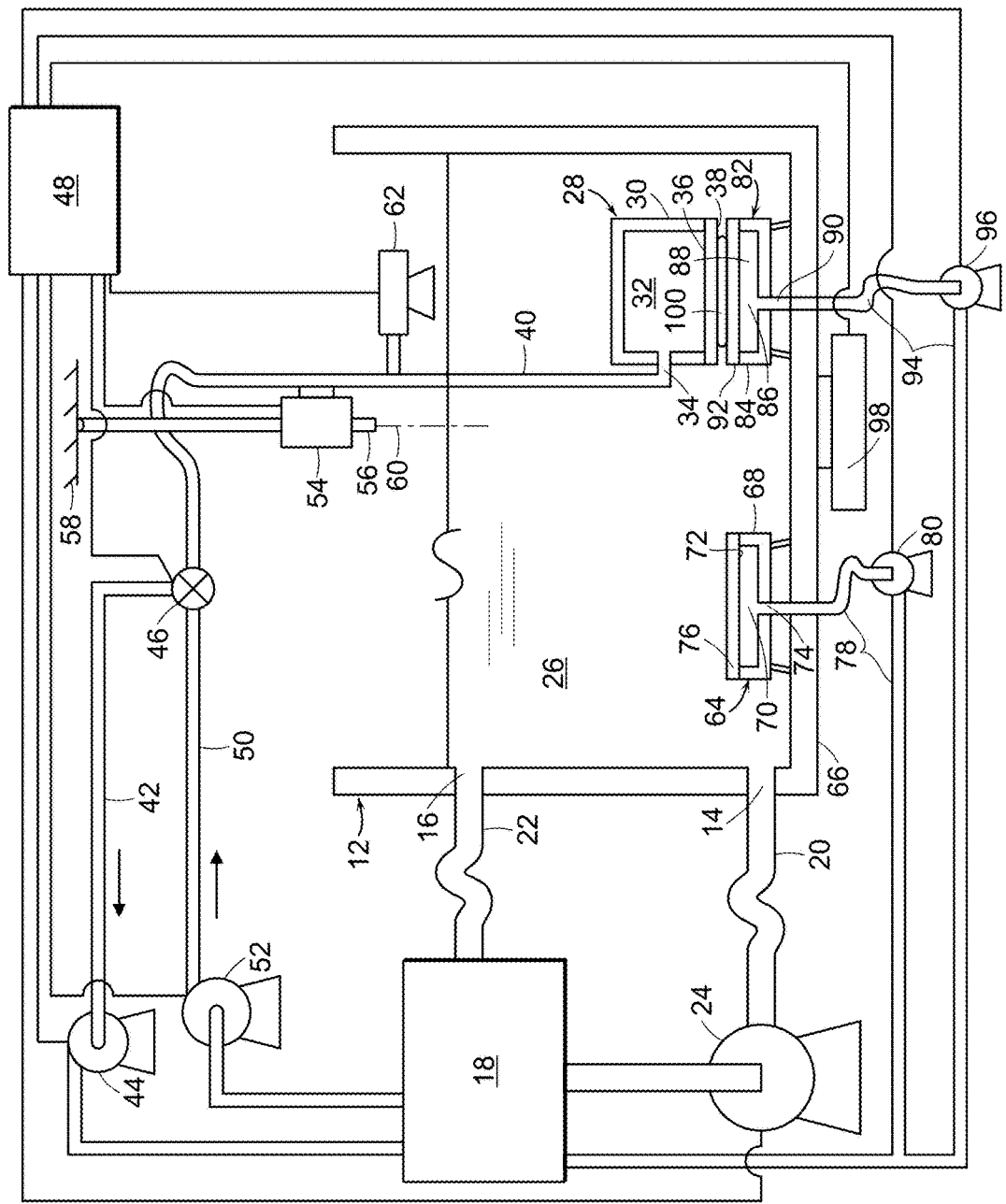
FIG. 8 is the embodiment of the device of FIG. 7, wherein the gripper has been lowered to the build support to thereby place the aggregation of cells on the build membrane.

As shown in FIG. 8, micromanipulator 54 is then actuated to move along the major longitudinal axis 60 of post 56, thereby lowering visualization device 62 and gripper 28 until aggregation of cells 100 is adjacent build membrane 92. Perfusate 26 is directed from assembly vessel 12 through build membrane 92 and through build support housing 84 and conduit 94 by pump 96 back to perfusate source 18 at a rate sufficient to cause aggregation of cells 100 to be retained at build membrane 92. The rate of flow of perfusate from assembly vessel 12 across aggregation of cells 100 and build membrane 92 into build housing 84 is also sufficient to sustain the cells with sufficient nutrients and oxygen.

Three-way valve 46 is then actuated to terminate flow of perfusate 26 from assembly vessel 12 through gripper membrane 38 and gripper housing 30, thereby terminating the force of flow through gripper membrane 38 that causes adherence of aggregation of cells 100 to gripper membrane 38. Optionally, three-way valve 46 is actuated to provide fluid communication between conduit 50 and pump 52, thereby reversing the flow of perfusate 26 so that, rather than perfusate 26 being directed from gripper 28 through perfusate source 18, perfusate 26 is directed from perfusate source 18 through pump 52, three-way valve 46 and gripper 28 into assembly vessel 12, providing a direction of flow that directs aggregation of cells 100 away from gripper membrane 38. Alternatively, when a peristaltic, or positive displacement valve is employed, a three-way valve is not necessary, and flow through conduit can be stopped or reversed simply by stopping or reversing operation of the peristaltic or positive displacement pump.

Figure 9:
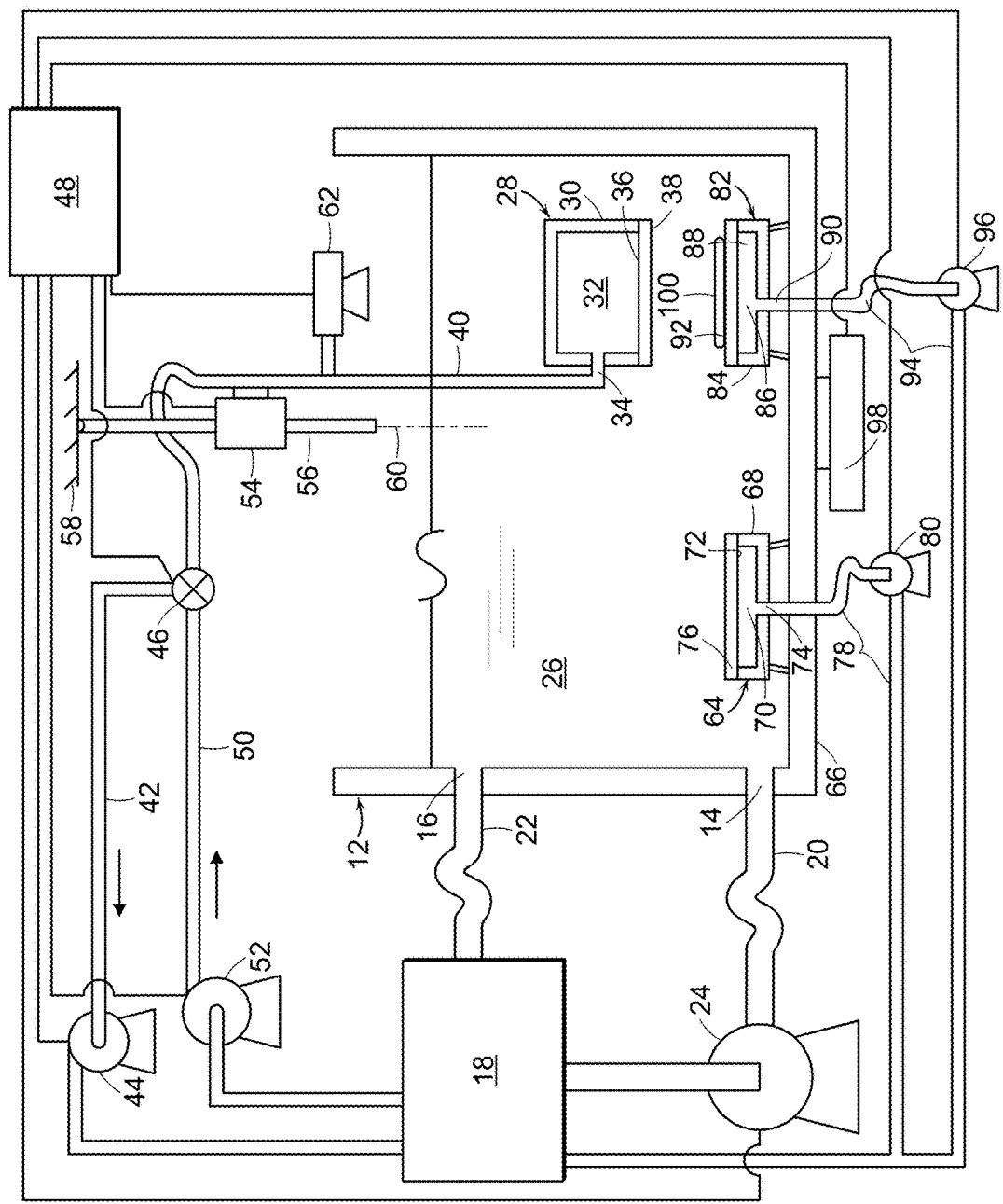
FIG. 9 is the embodiment of the device of FIG. 8, wherein the gripper has been raised after release of the aggregation of cells on the build support membrane.

As can be seen in FIG. 9, micromanipulator 54 is then actuated to move along longitudinal axis 60 of port 56, thereby raising visualization device 62 and gripper away 28 from build support 82, leaving aggregation of cells 100 at build membrane 92. At this time, if not already done, three-way valve 46, or other suitable means, depending on the type of pump employed, can be actuated to terminate flow of perfusate 26 from perfusate source 18 to gripper 28, if the three-way valve 46 is set to cause perfusate to be so directed.

Figure 10:
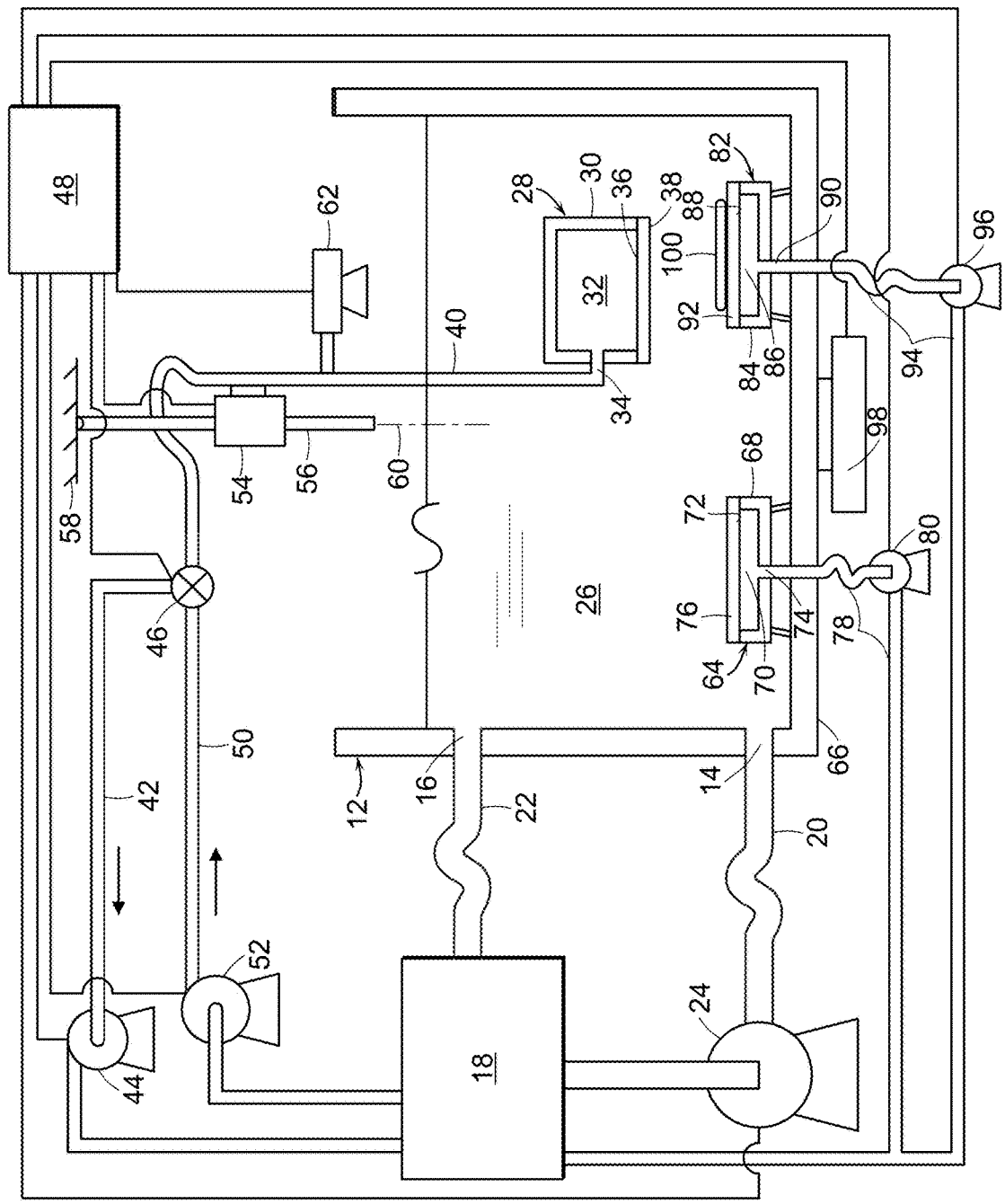
FIG. 10 is the embodiment of the device of FIG. 9, wherein the vessel has been moved in a horizontal plane to prepare the gripper for rotation about the vertical axis prior to gripping a second agglomeration of cells.
Figure 11:
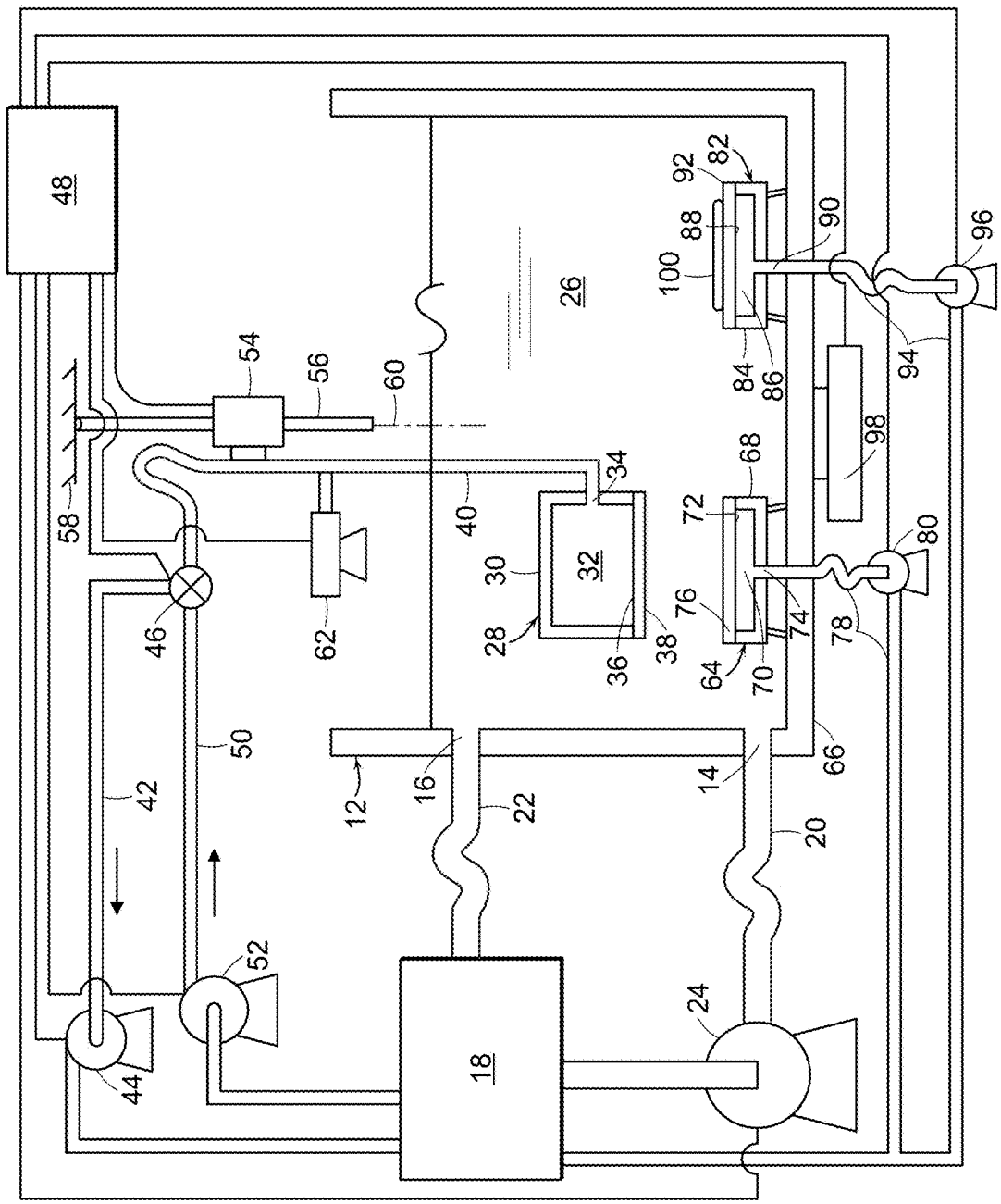
FIG. 11 is the embodiment of the device of FIG. 10, wherein the gripper has been rotated about the vertical axis to thereby align the gripper with the staging support for gripping the second agglomeration of cells.

As shown in FIG. 10, assembly vessel support 98 is then actuated to move assembly vessel 12 and, consequently, staging support 64 and build support 82, in a plane essentially transverse to the longitudinal axis 60 of post 56. As shown in FIG. 11, micromanipulator 54 is actuated to cause rotation of micromanipulator 54 about the major longitudinal axis 60 of post 56, thereby aligning gripper membrane 38 with staging support 64.

Figure 12:
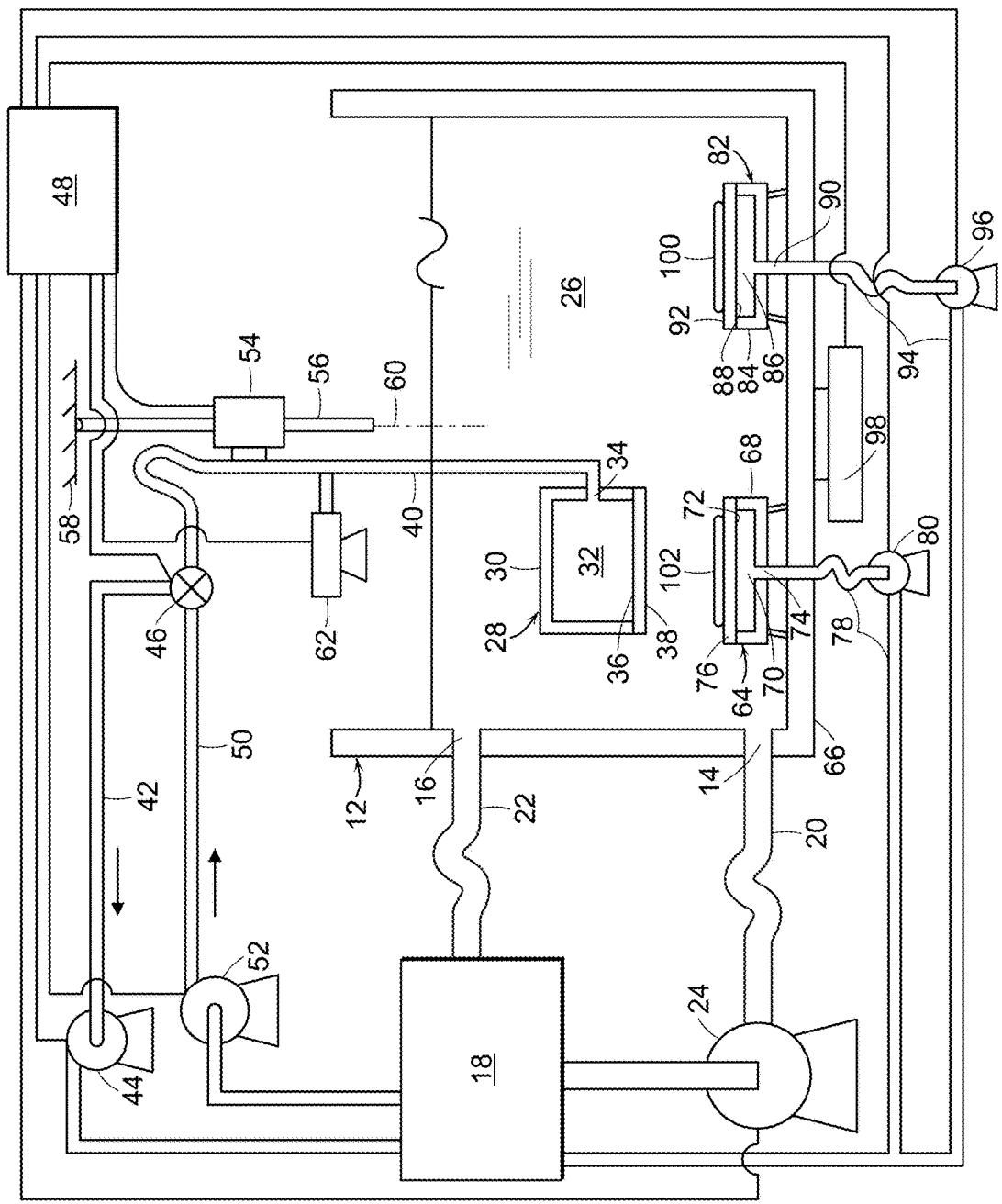
FIG. 12 is the embodiment of the device of FIG. 11, wherein a second agglomeration of cells has been placed on the staging support.

As shown in FIG. 12, the next, or second, aggregation of cells 102, either by prior placement of second aggregation of cells 102 on staging support 69 previously employed, or by actuation of assembly vessel support 98, is vertically aligned with assistance of visualization device 62 with gripper membrane 38.

Figure 13:
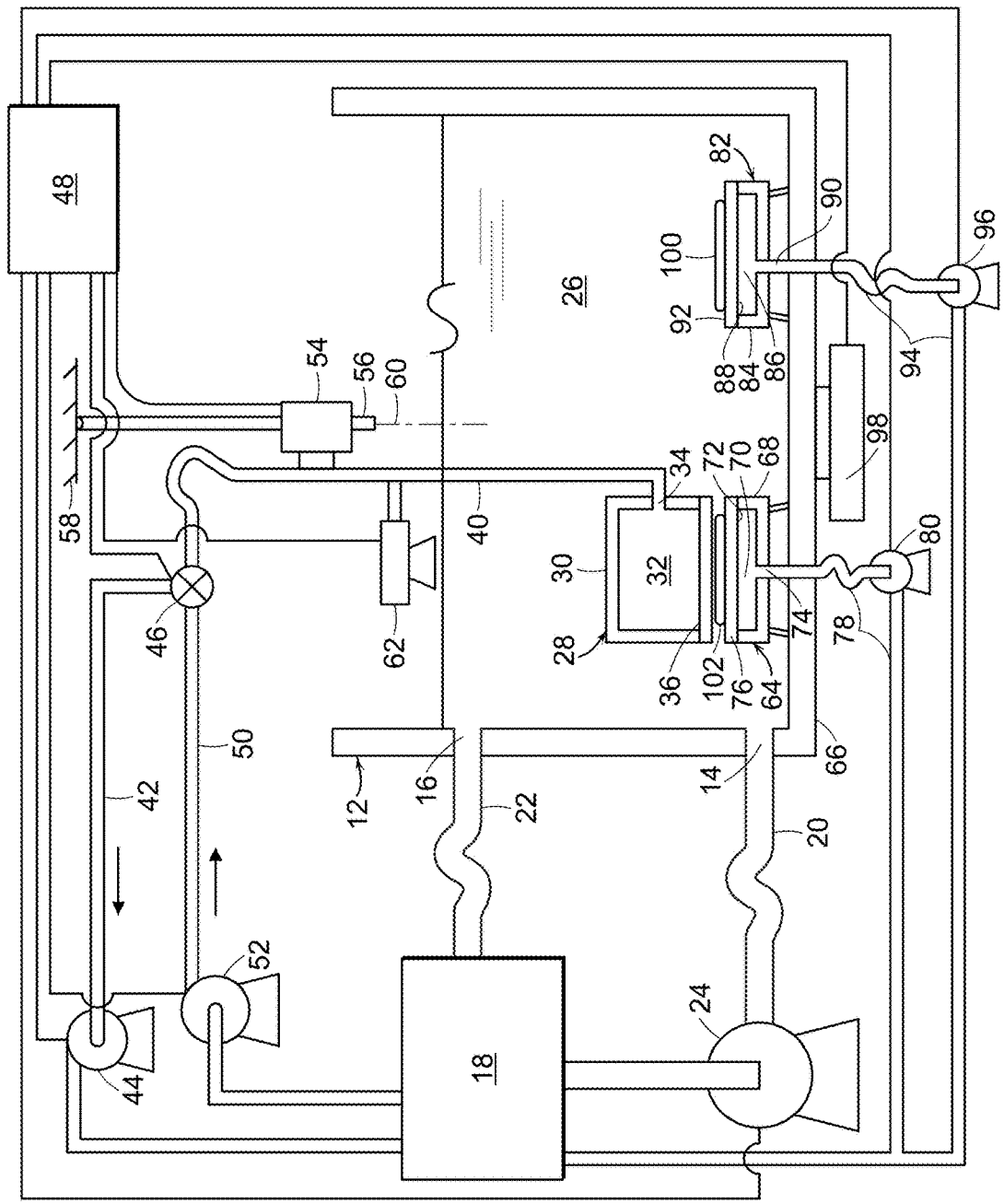
FIG. 13 is the embodiment of the device of FIG. 12, wherein the gripper has been lowered to the second agglomeration of cells at the staging support.

As shown in FIG. 13, gripper 28 and, thereby, gripper membrane 38 are lowered by actuation of micromanipulator 54 to cause gripper membrane 38 to contact second aggregation of cells 102 at staging membrane 76. Three-way valve 46, or other suitable valve, depending on the type of pump used, is then actuated to cause perfusate 26 to be directed from assembly vessel 12 through gripper membrane 38 and gripper housing 30 through conduits 40, 42 and pump 46 to perfusate source 18 at a rate greater than the rate at which perfusate 26 is directed through staging membrane 76, pump 80 and conduit 78 to perfusate source 18, thereby causing second aggregation of cells 102 to preferentially adhere to gripper membrane 38. Also, the rate at which perfusate 26 is directed across second aggregation of cells 102 and gripper membrane 38 is sufficient to sustain second aggregation of cells 102.

Figure 14:
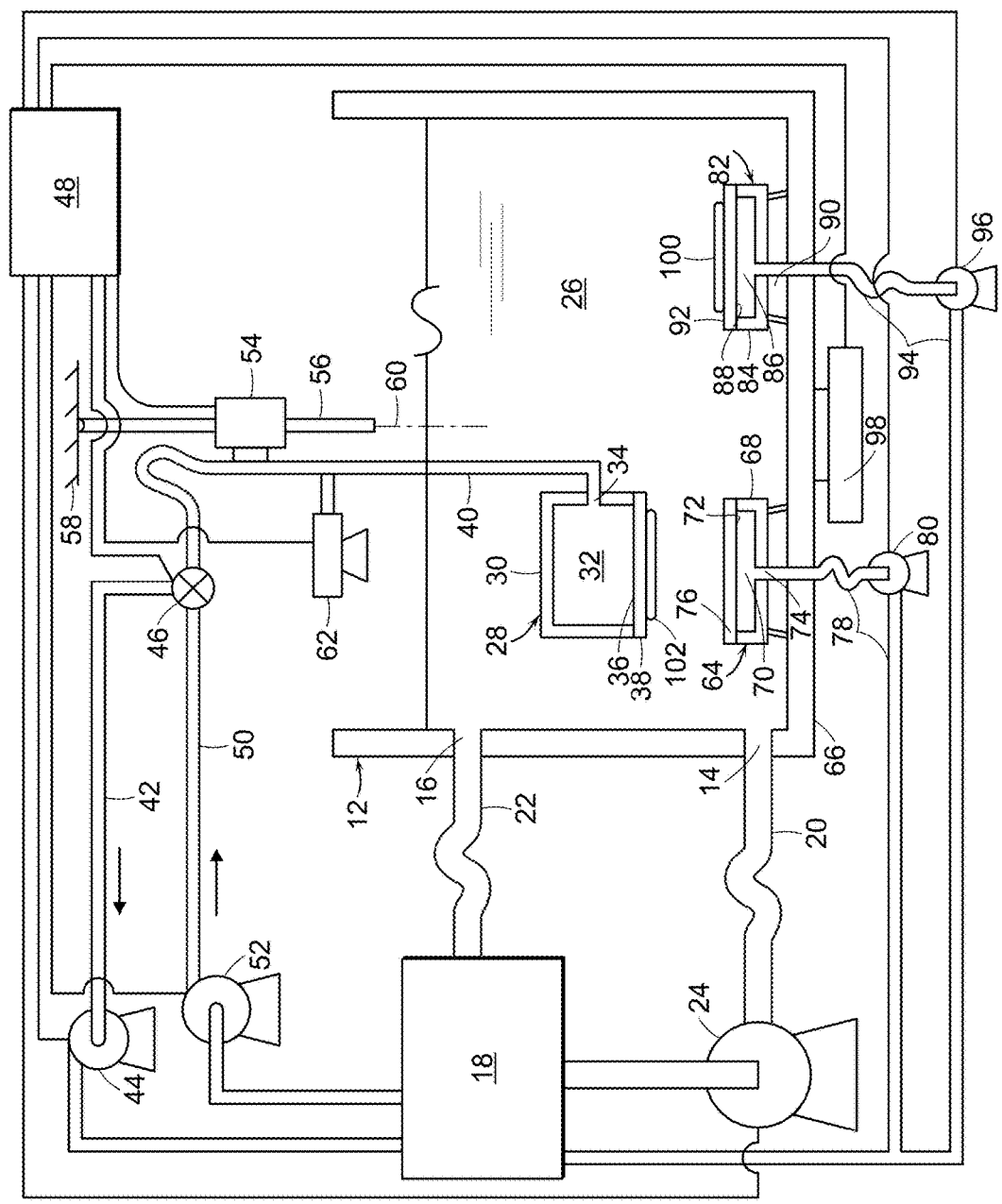
FIG. 14 is the embodiment of the device of FIG. 13, wherein the gripper has been raised while gripping and lifting the second agglomeration of cells off of the staging support.
Figure 15:
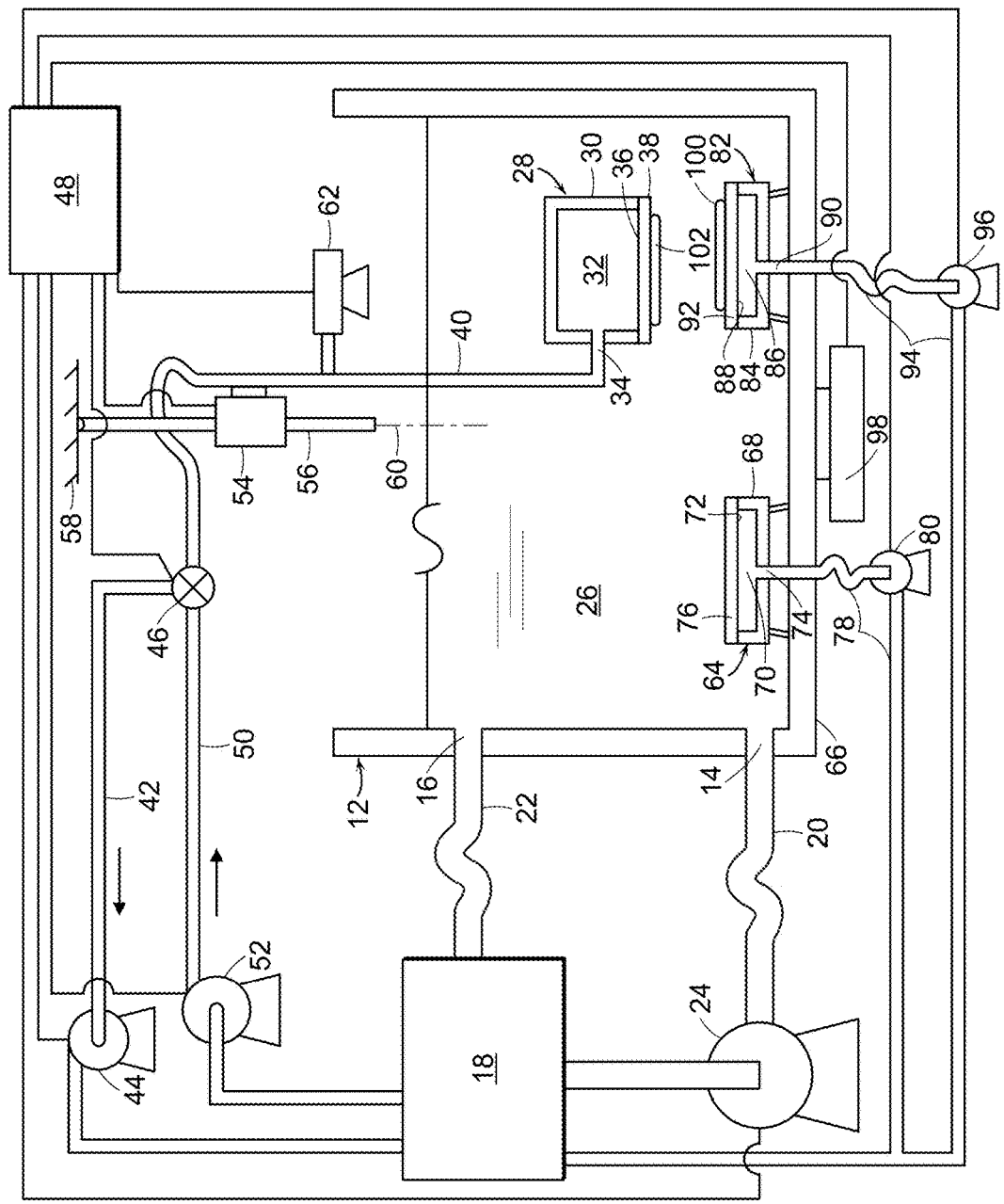
FIG. 15 is the embodiment of device of FIG. 14, wherein the gripper has been rotated about a vertical axis to bring the second aggregation of cells within the proximity of the build support and the first aggregation of cells.
Figure 16:
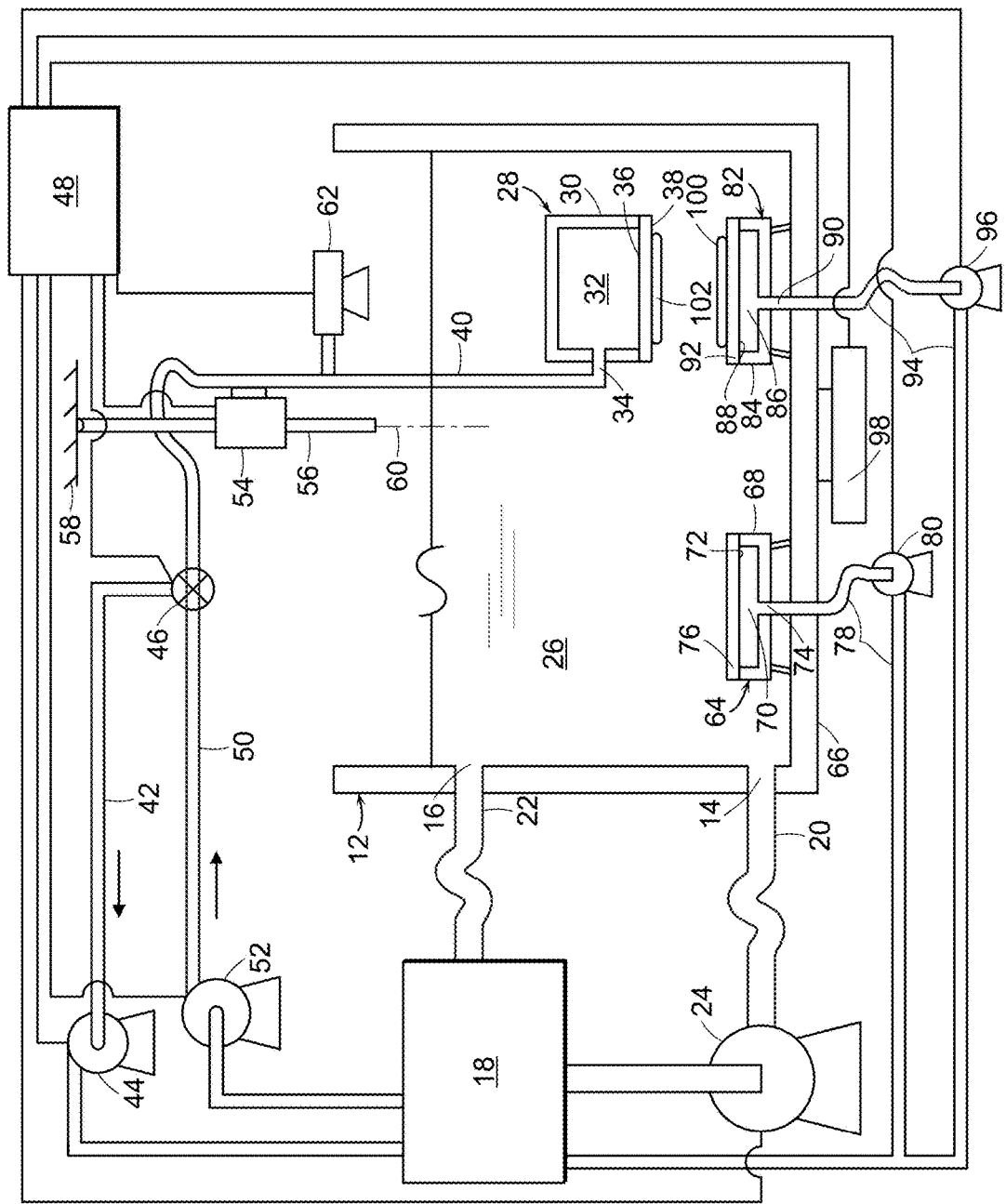
FIG. 16 is the embodiment of the device of FIG. 15, wherein the assembly vessel has been moved in a horizontal plane to align the gripper and second aggregation of cells within the build support and first aggregation of cells.

As shown in FIG. 14, micromanipulator 54 is then actuated to raise gripper 28, with second aggregation of cells 102 adhering to gripper membrane 38, away from staging membrane 76. Micromanipulator 54 is then actuated to rotate about the major longitudinal axis 60 of post 56, to thereby bring gripper 28 and second aggregation of cells 102 within the proximity of first aggregation of cells 100 previously deposited at build membrane 92, as shown in FIG. 15. Assembly vessel support 98 is then actuated to cause alignment, with the assistance of visualization device 62 and controller 40, of first aggregation of cells 100 at build membrane 92 with second aggregation of cells 102 at gripper membrane, as shown in FIG. 16.

Figure 17:
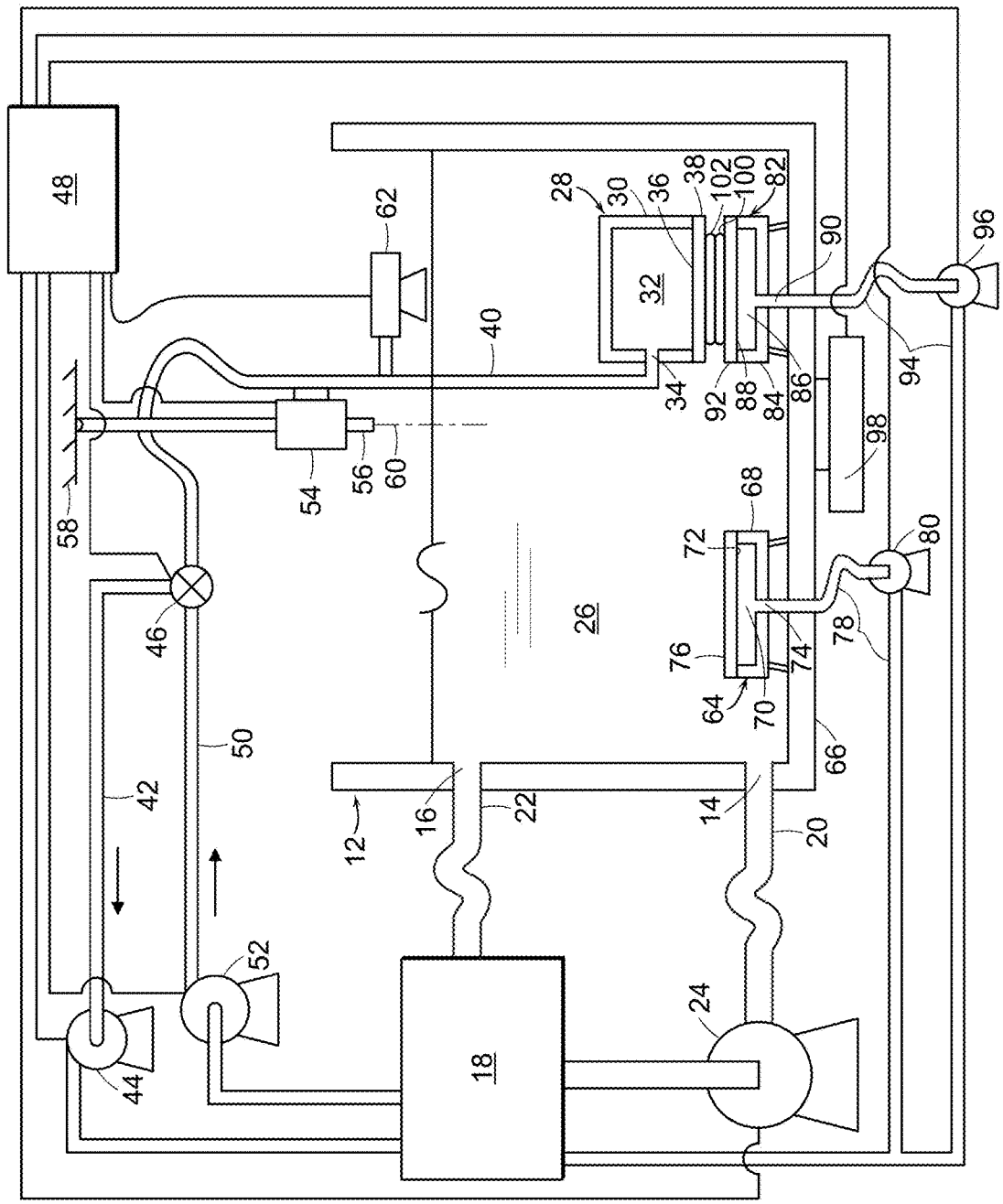
FIG. 17 is the embodiment of the device of FIG. 16, wherein the gripper and the second aggregation of cells have been lowered vertically to bring the second aggregation of cells into contact with the first aggregation of cells.

Gripper 28, with second aggregation of cells 102, is then lowered until second aggregation of cells 102 is contacting first aggregation of cells 100, as shown in FIG. 17.

Figure 18:
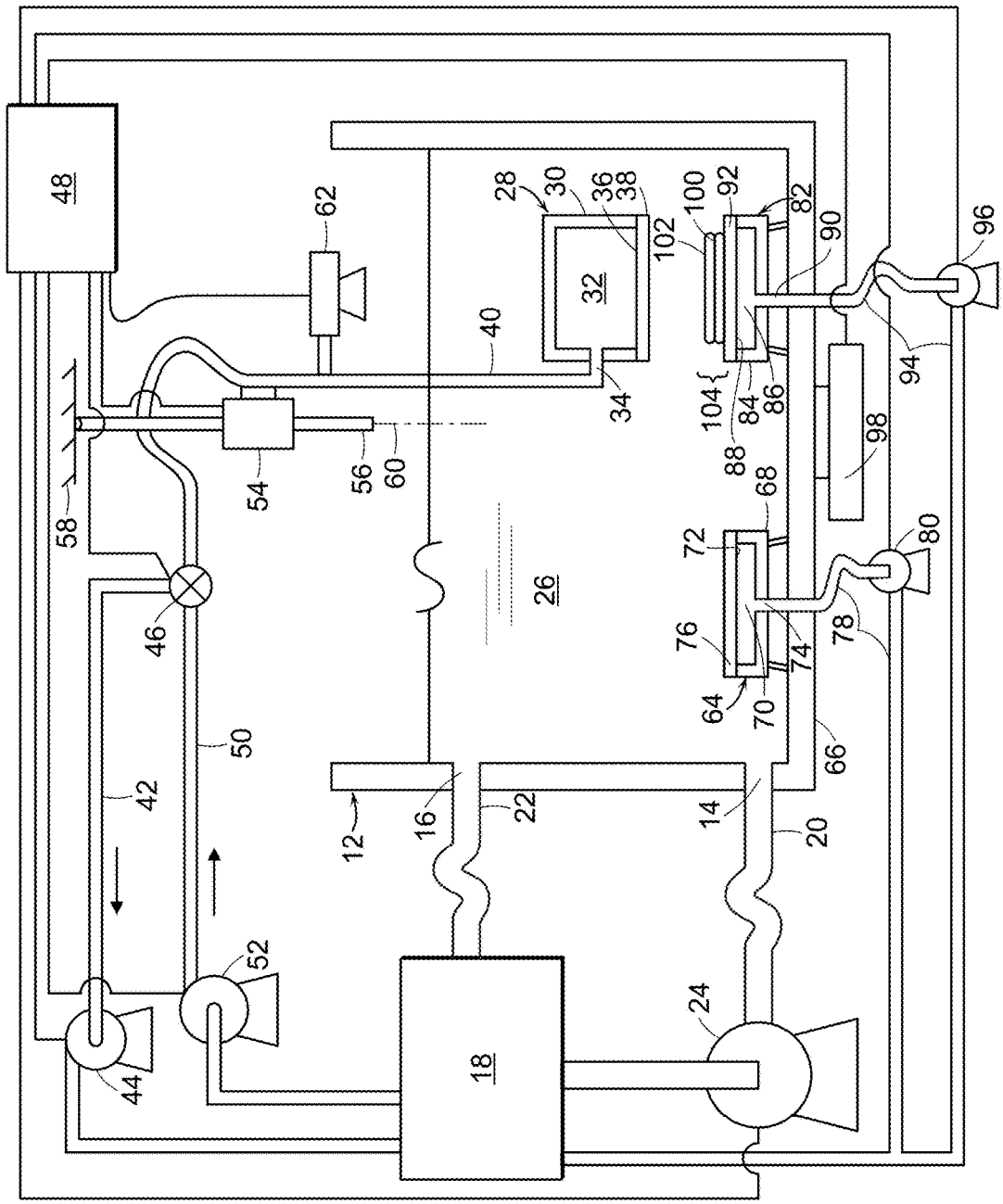
FIG. 18 is the embodiment of the device of FIG. 17, wherein the gripper has been vertically raised to leave the second aggregation of cells on the first aggregation of cells, thereby forming an assembly of aggregations of cells of the invention.

Three-way valve 46, or another type of valve, as appropriate, is then actuated again, as described previously, with respect to the first aggregation of cells 100 placed at build membrane 92 and, as shown in FIG. 18. Alternatively, pump 44 is shut off. In either case, second aggregation of cells 102 is released from gripper membrane 38, or drawn away from gripper membrane 38 by flow of perfusate 26 directed across second aggregation of cells 102, first aggregation of cells 100, and build membrane 92 into build support chamber 86 and back to perfusate source 18. Gripper 28 is then raised, leaving second aggregation of cells 102 upon first aggregation of cells 100, thereby assembling aggregations of cells 104 in a stack on build support 82.

The above process is then repeated to build a stack of aggregations of cells 104 at build support 82 until a suitable number of aggregations of cells have been assembled on build support 82. The number of aggregations of cells assembled on build support 82 is indefinite. For example, one strategy is to define the minimum number that defines a stack which is two, such as for an artificial cornea. Another embodiment, for example, would be building a liver for humans. The human liver has about 240 billion cells. A large honeycomb part may have close to 10 million cells, so to build a liver would require picking and placing about 24,000 parts of this size. Larger parts would mean fewer stacks. A third embodiment would be to build a "mega" organ not for transplantation but rather for the in vitro synthesis and secretion of valuable products, such as recombinant proteins. These man-made mega organs would be like biomanufacturing facilities and so could have even more stacks.

Following assembly of a suitable number of layers of aggregations of cells, the assembly can be removed from assembly vessel 12 for suitable use. Alternatively, the assembly of aggregations of cells 104 can remain within vessel and perfused by perfusate that is conducted through assembly of aggregations of cells 104, such as through openings defined by the aggregations of cells 104 assembled on build support 82 through build support housing 84 and back to perfusate source 18, thereby allowing the assembly of aggregations of cells 104 to remain in place by virtue of the flow of perfusate 26 from assembly vessel 12 through build support 82 and providing sufficient nutrients to maintain the assembled aggregations of cells 104 for a period of time sufficient to cause the assembly of aggregations of cells 104 to fuse. The fused assembly of aggregations of cells 104 can then be removed from assembly vessel 12 for subsequent processing and use, such as surgical use as tissue.

In one embodiment, the assembly of aggregations of cells 104 is conducted in a manner to cause openings defined by the aggregations of cells to substantially align. In another embodiment, the aggregations of cells are stacked in a manner that does not cause the openings defined by each aggregation of cells to be aligned. In a still further embodiment, different shapes of aggregations of cells are assembled to thereby cause formation of a stack of aggregations of cells that assumes a three-dimensional character, such as that of a frustum, pyramid, or other three-dimensional shape (not shown) that, upon fusion of the layers of aggregations of cells assembled, will form a unitary three-dimensional tissue suitable for use as, for example, replacement tissue of a body part.

Figure 19:
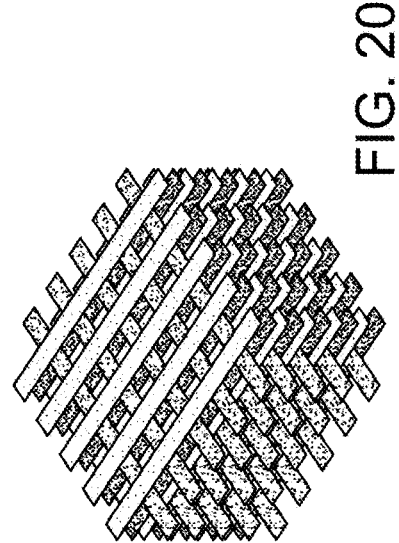
FIG. 19 is a perspective view of an assembly of aggregations of adherent cells of one embodiment of the invention. Stacking and alignment of honeycomb-shaped parts creates channels for perfusion.
Figure 20:
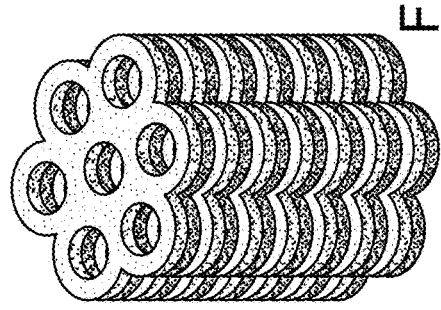
FIG. 20 is a perspective view of one embodiment of an assembly aggregation of cells of the invention that includes rod-shaped building parts that define channels for perfusion.
Figures 21A, 21B, 21C, 21D:
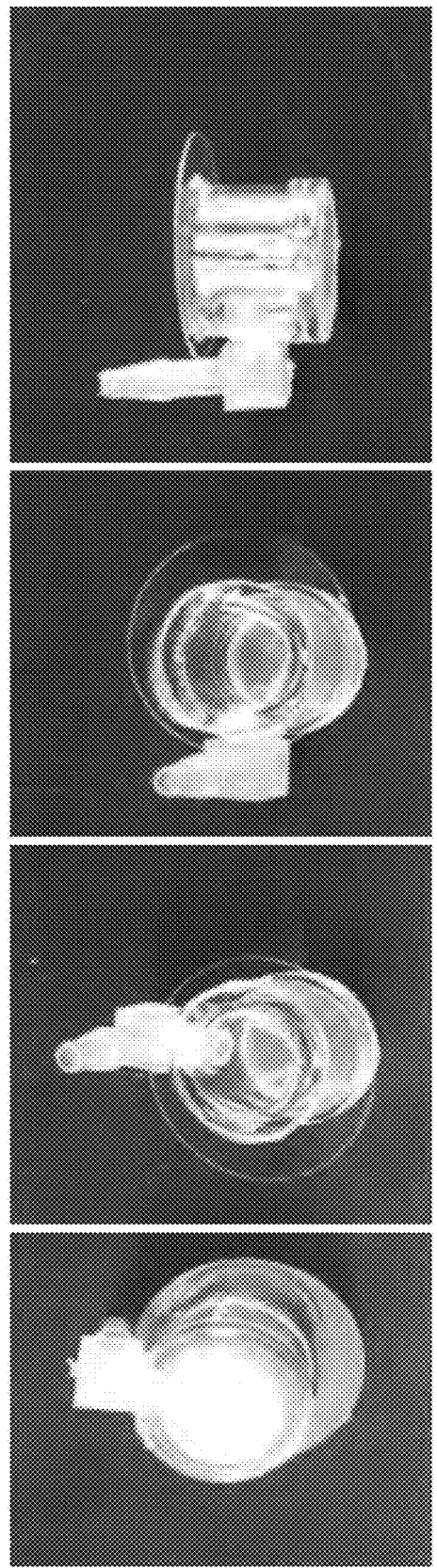
FIGS. 21A-21D are photographs of different views of an embodiment of a gripper suitable for use in the device of the invention. The gripper includes a round membrane (dia 12 mm, 3 μm pores). The different views show membrane gripping surface (FIG. 21A) and side view of capped polystyrene cylinder with connector for pump tubing (FIG. 21D).

FIG. 19 shows a schematic of how vascular channels are formed when honeycomb parts are stacked. Alternatively, as shown in FIG. 20, vascular channels can be created by cross stacking building parts in the shape of rods as described. Flow rates of $Q=1$ cm$^3$/min are sufficient for griping the structures without any damage. Where permeability of membrane is $k=n\pi d^4/128=6\times10^{-10}$ cm$^2$, for example, the pressure drop across the membrane is estimated to be $\Delta p=Q\mu L/kA=102$ Pa. Hence, negative pressures of about 100 Pa typically are enough to grip H35 spheroids. These pressure drops not enough to induce rupture of the microtissues.

The device and method of the invention will now be demonstrated by the following experimental demonstration, which is not intended to be limiting in any way.

EXEMPLIFICATION

Example 1

Materials and Methods
Micro-Molded Hydrogels and Microtissue Formation

Agarose gels were cast from 3D Petri Dish® micro-molds (Microtissues, Inc., Providence, R.I.). Powder UltraPure™ Agarose (Invitrogen, Carlsbad, Calif.) was sterilized by autoclaving and dissolved via heating in sterile water to 2% (weight/volume). Molten agarose was pipetted into each micro-mold and air bubbles were removed by agitation with a sterile spatula. After setting, gels were separated from the micro-mold using a spatula, transferred to twelve-well tissue culture plates, and equilibrated for at least 4 hours with several changes of culture medium. Micro-molds with two different recess geometries were used to produce agarose gels to create spheroid or toroid microtissues. Round recesses for spheroids were 800 µm in diameter and contained 81 recesses per gel. Toroidal recesses were 1400 µm in diameter with a central agarose peg of 600 µm and contained 36 features per gel.

Rat hepatoma (H35) and human ovarian granulosa (KGN) cells were expanded in Dulbecco's Modified Eagle Medium (DMEM) (Invitrogen) supplemented with 10% fetal bovine serum (FBS)(Thermo Fisher Scientific, Waltham, Mass.) and 1% penicillin/streptomycin (Sigma-Aldrich, St. Louis, Mo.). Cultures were maintained in a 37° C., 10% $CO_2$ atmosphere. Cells were trypsinized, counted, and re-suspended to the desired cell density for each experiment. 190 µL of cell suspension was pipetted into the rectangular seeding chamber above the recesses of each micro-molded agarose gel. Spheroid gels were each seeded at a concentration of 1,250 cells per spheroid feature. Toroid gels were each seeded at concentrations varying from 25,000 to 35,000 cells per toroid feature. Samples were then incubated for approximately twenty minutes to allow cells to settle into recesses before 2 mL of medium was slowly added to each well. Medium was exchanged every other day.

Live-Dead and Cell Tracker Staining

For Live-Dead staining, microtissues were incubated with a mixture of 2 mL phosphate-buffered saline (PBS) with 4 µM of ethidium homodimer-1 and 1 µM calcein AM (Invitrogen) for 75 minutes at 37° C. Microtissue viability was assessed via fluorescent imaging using a Zeiss Axio Observer Z1 equipped with an AxioCam MRm camera with AxioVision Software (Carl Zeiss Micro-Imaging, Thornwood, N.Y.) and an X-Cite 120 fluorescence illumination system (EXFO Photonic Solutions, Ontario, Canada).

For Cell Tracker staining, cells were washed with serum-free medium and incubated for 45 minutes in either DMEM with 5 µM CellTracker™ Green (Invitrogen) or DMEM with 5 µM CellTracker™. Plates were washed with PBS and the labeled cells were trypsinized, counted and seeded into micro-molds to form labeled microtissues.

Fabrication of Device Instrument

The bio-gripper head of the device instrument, shown in FIGS. 21A-21D was fabricated using a Millicell cell culture insert (EMD Millipore, Billerica, Mass.) (12 mm diameter, 10 mm in height) with a polycarbonate membrane with track-etched 3-micron pores. The three small feet on the bottom of the cylindrical insert were removed. A 4-mm hole was drilled into the side of the insert and a polypropylene elbow joint fitting (2.4 mm ID)(Cole-Parmer Instrument Co., Chicago, Ill.) was connected using plastic cement (The Testor Corp., Rockford, Ill.). The top or open end of the insert was sealed with a standard 18 mm circular micro cover glass (VWR Scientific, Inc., West Chester, Pa.) using epoxy (ITW Devcon, Danvers, Mass.). The elbow joint was connected to a segment (14 cm) of stiff polystyrene tubing that was attached to a manual x, y, z micromanipulator (Narishige, Nikon, Japan) mounted on a Nikon Diaphot inverted microscope with manual x, y stage control and its condenser removed. The bio-gripper's micromanipulator was mounted directly above and in line with the objectives. The other end of the polystyrene tube was fitted with a male-male tubing joint that was connected to tubing run through a Multistaltic® peristaltic pump (Haake Buchler Instruments, Inc., Saddle Brook, N.J.) capable of reversible flow rates up to 2 mL/minute. The other end of the tubing was placed into the build chamber, a 150-mm Petri dish containing cell culture medium, thus creating a closed system for recirculation of culture medium during operation of the device.

The device was operated as follows. Microtissues (spheroids or toroids) released from their micro-molds were deposited into the build chamber and brought into view using the microscope's x, y stage. The bio-gripper head, submerged in cell culture medium, was lowered down onto the microtissue. Proximity of microtissue and the membrane of the gripper head were evident when both were in focus. The peristaltic pump was run at 1 mL/min to grip tissues. After gripping, the bio-gripper head was raised, with both the microtissue of interest and the membrane moving out of focus.

To place the microtissues, the microscope's x, y stage was adjusted so that the intended target was brought into position under the bio-gripper head with gripped microtissue. The head was lowered, and when it had reached the appropriate distance on the z-axis, flow across the membrane was reversed to facilitate release of the microtissue. Bio-gripper heads were exchanged with each experiment to mitigate the effect of membrane clogging from debris. Side-views of the microtissue being lowered onto its target were obtained using a dissecting microscope mounted perpendicular to the z-axis and was useful for more precise control of the distance between gripped microtissue and target.

Instrument Fabrication

Figure 22:
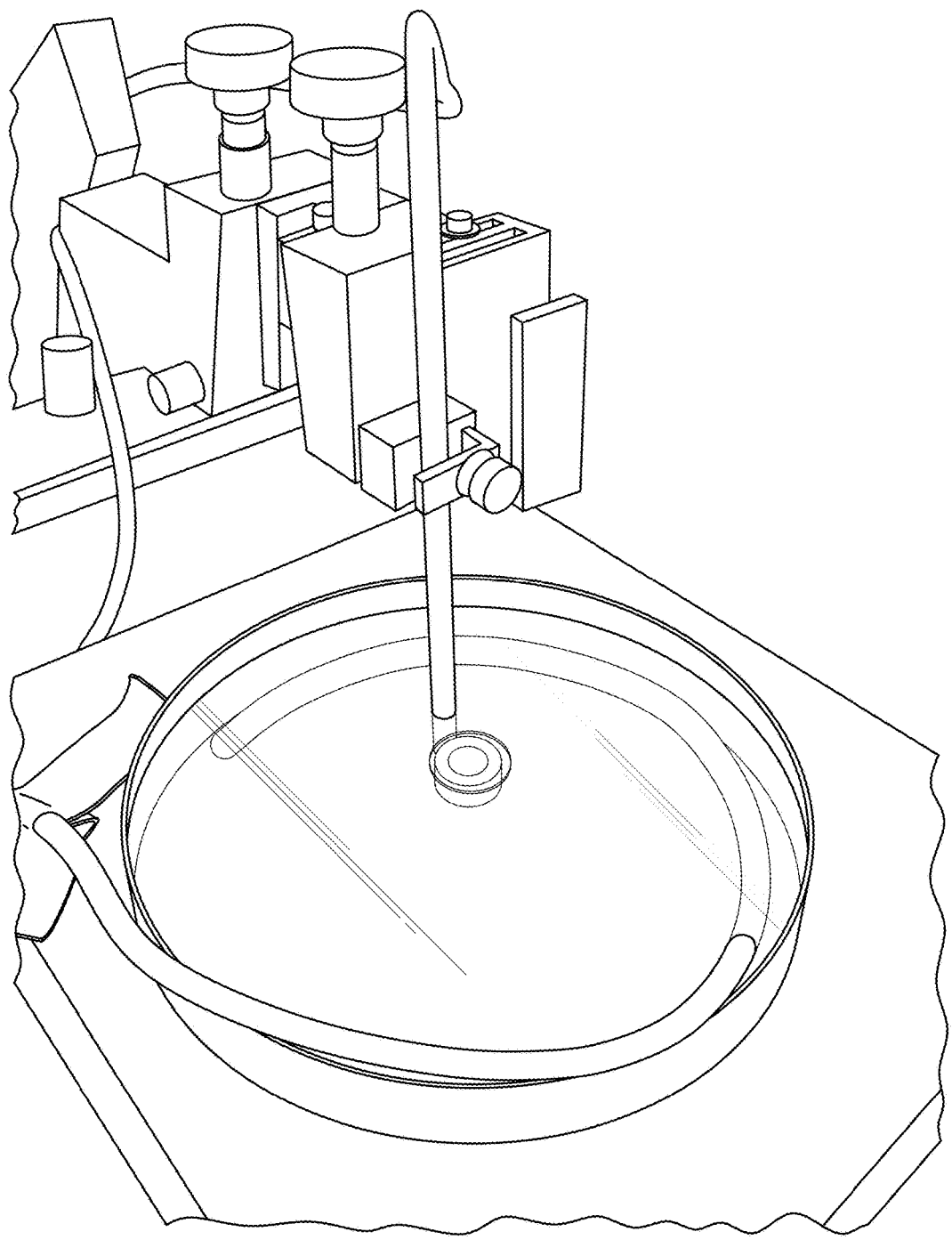
FIG. 22 is a photograph of another embodiment of the device of the invention. Shown is the bio-gripper head held in place by a manual x, y, z micromanipulator positioned over the objectives of an inverted microscope. The bio-gripper head (or gripper) is immersed in the cell culture medium of the build area (lid removed) and is attached to a peristaltic pump that creates controllable fluid suction to grip and dispense microtissues (aggregations of adherent cells). A microtissue to be gripped is positioned under the bio-gripper by moving the build area using the x, y (horizontal) microscope stage. The bio-gripper is then lowered along its z (vertical) axis to contact the microtissue and fluid suction grips the microtissue to the membrane. The bio-gripper with attached microtissue is retracted and the microscope stage moved to the target. The bio-gripper is lowered and fluid flow reversed to dispense the microtissue on its target.
Figures 24A, 24B, 24C, 24D:
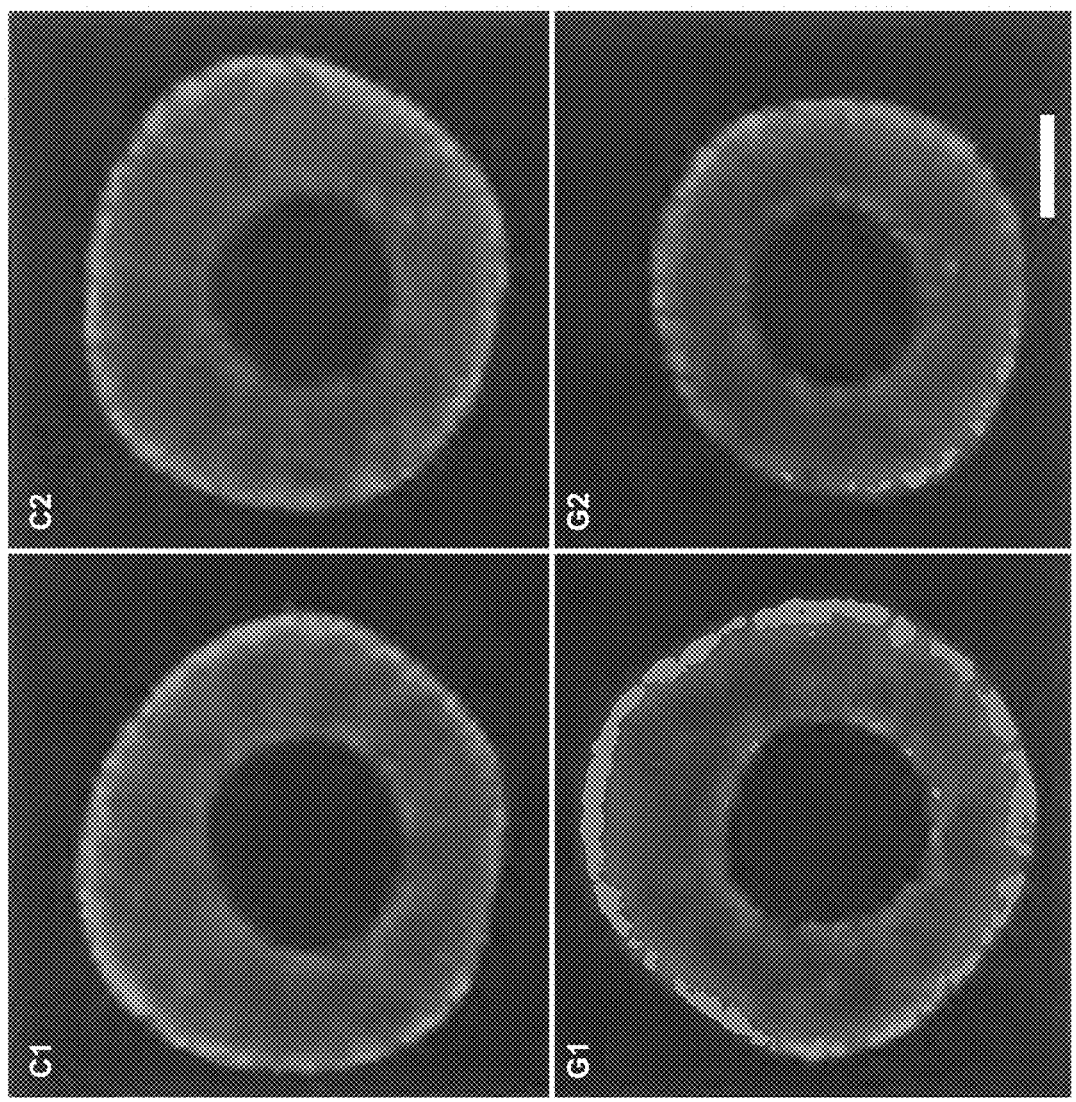
FIGS. 24A-24D are photographs of live/dead staining of ungripped control (FIGS. 24A, 24B) and gripped (FIGS. 24C, 24D) KGN toroids, 25,000 cells/toroid. Scale bar 200 microns.

To build a manually operated device instrument, the condenser of an inverted microscope was removed and mounted directly above the objectives an x, y, z micromanipulator holding a bio-gripper head (FIG. 22). The bio-gripper head was fabricated from a cylindrical polystyrene cell culture insert with a membrane (3 µm diameter pores). The insert top was capped off with a glass coverslip and a side port added to attach tubing (FIGS. 21A-21D). The controllable fluid suction force of the bio-gripper head was created by the action of a peristaltic pump pulling culture medium through the membrane. The porous membrane (of area $A=\pi D^2/4=0.6$ cm$^2$, pore size d=3 µm, thickness L=22 µm and pore density $n=3\times10^6$ pores/cm$^2$) was transparent when wet enabling visualization of the microtissue when gripped. Permeability of the membrane was approximately $k=n\pi d^4/128=6\times10^{-10}$ cm$^2$, and the pressure drop across the membrane at low flow rates (Q=1 cm$^3$/min) were estimated to be $\Delta p=Q\mu L/kA=102$ Pa. The bio-gripper head was a modular piece that was easily exchanged and could be custom designed for microtissues of varying sizes and shapes Gripped Microtissues were Viable To determine if gripping altered the viability of microtissues, H35 spheroids (1250 cells/spheroid) were gripped, moved and dispensed into dishes coated with agarose to prevent spheroid adhesion. Control ungripped spheroids were kept in parallel dishes and subjected to all the same treatments except gripping. Spheroids were then stained with Live/Dead (FIG. 23A-23F). From these images, there was no significant difference in the viability between gripped and non-gripped spheroids.

To determine if larger more complex structures could be gripped, toroids of KGN cells (25,000, 30,000, and 35,000 cells/toroid) were made. The toroids were loaded into the build area, gripped and deposited into an agarose coated culture dish submerged in the build area. Control (non-gripped toroids) and gripped toroids were stained Live/Dead (FIGS. 23A-23F, 24A-24D). There was no breakage of the toroid structure and there were no differences in viability between gripped and control toroids at any of the seeding densities tested.

Large Sheets of Toroids were Formed and Gripped:

To determine if the device could safely manipulate even larger more complex microtissues, sheets of fused toroids were formed. After 15 hours of self-assembly, toroids (~30,000 to 40,000 cells/toroid) were released from their micro-molds into 60-mm dishes that had been coated with agarose. After the toroids settled, the dishes were tilted causing the toroids to collect on one side of the dish and contact each other. Twenty four later, the toroids had fused into a contiguous sheet of toroids. Gripping, moving and releasing these sheets did not fracture the sheet or alter its viability (FIGS. 25A-25D). The same flow rate (1 mL/min) was used to grip individual microtissues and the sheet of toroids. During the fusion process, the lumens of the toroids narrowed, less so for the toroids with 30,000 cells versus 40,000 cells.

Figure 27:
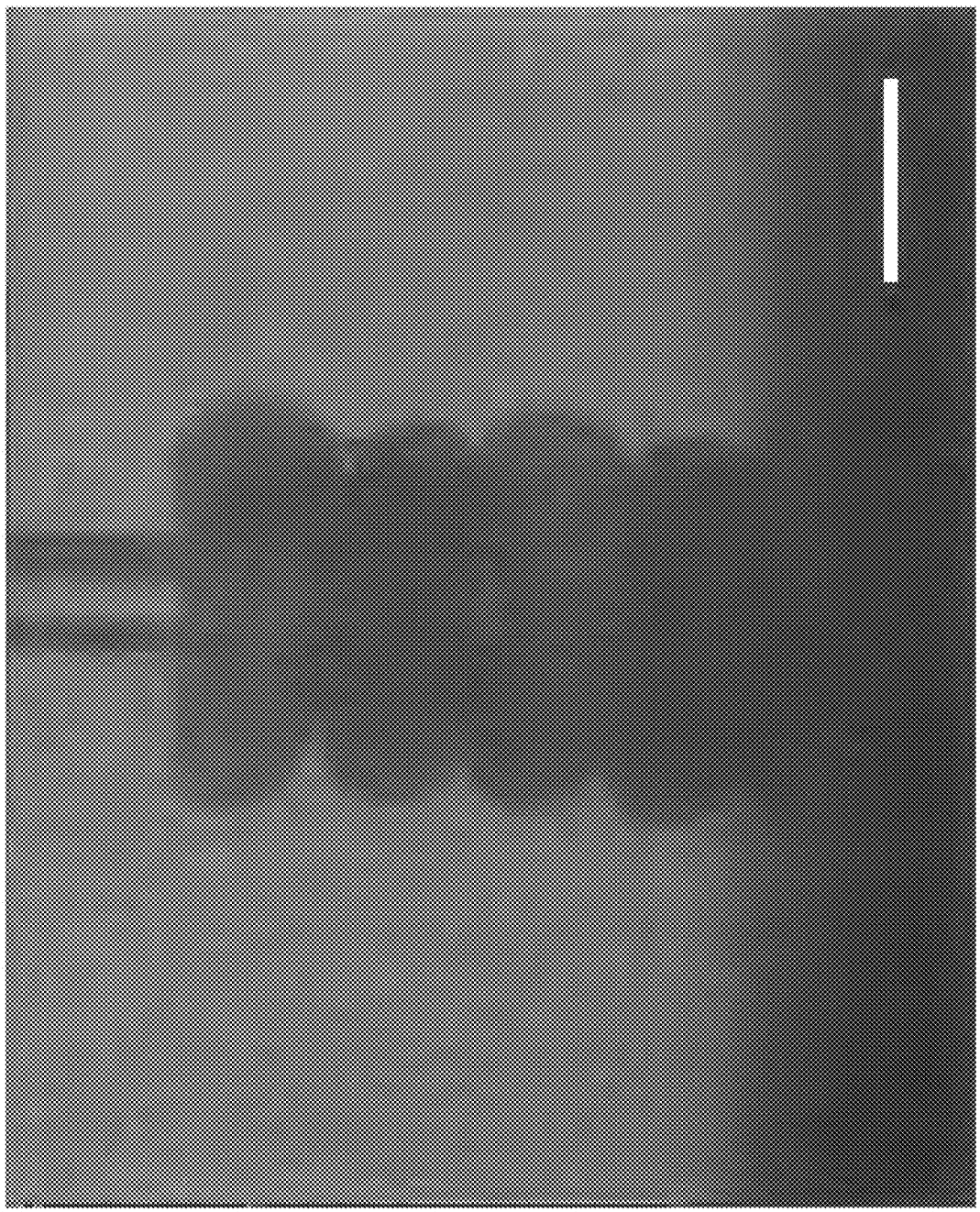
FIG. 27 is a photographic (Brightfield) image of four KGN toroids stacked on a 330-micron outer diameter capillary tube. Scale bar 300 microns.
Figure 28A:
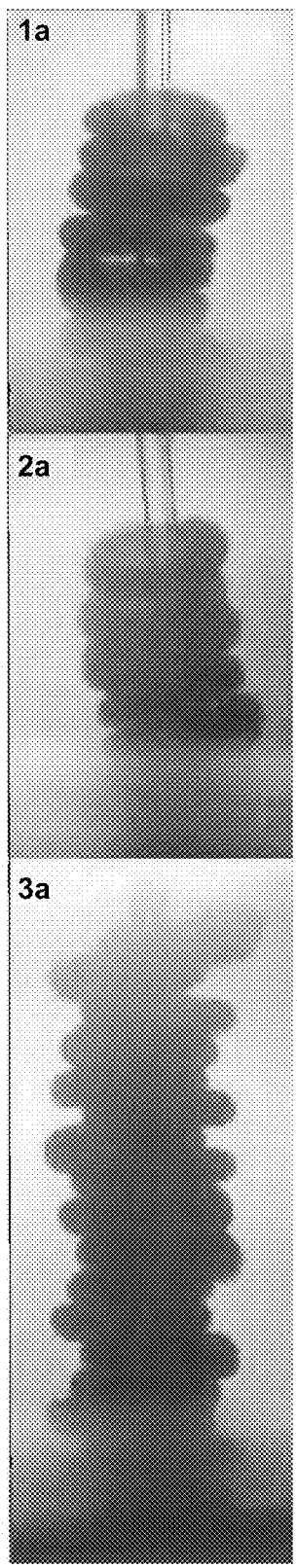
FIGS. 28A-28E are photographic grayscale brightfield side view images of a toroid stack around a 170-micron outer diameter capillary tube, demonstrating fusion of individual toroids into a single tissue over time (FIG. 28A=0 hrs, FIG. 28B=12 hrs, FIG. 28C=24 hrs, FIG. 28D=48 hrs, FIG. 28E=72 hrs). Scale bar 500 microns. This is new data not in original filing. Attached is the figure from our manuscript we are submitting, below is the figure legend.
Figure 28B:
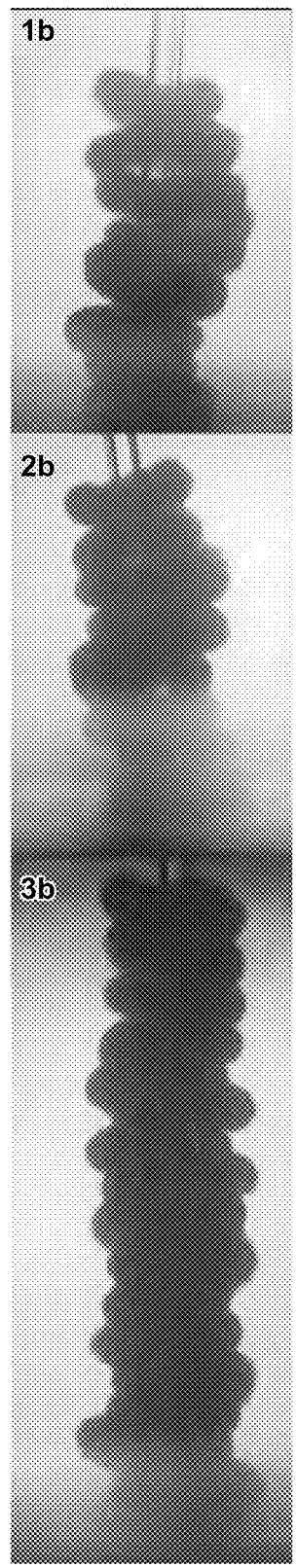
Figure 28C:
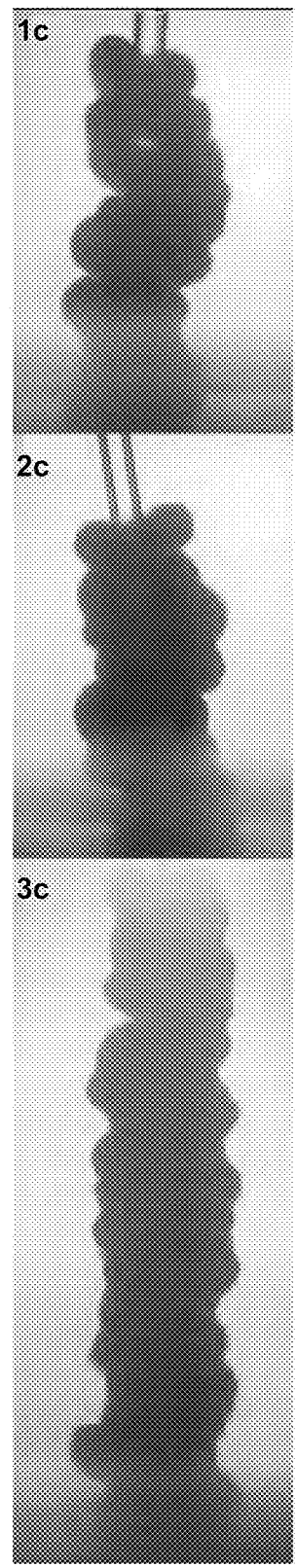
Figure 28D:
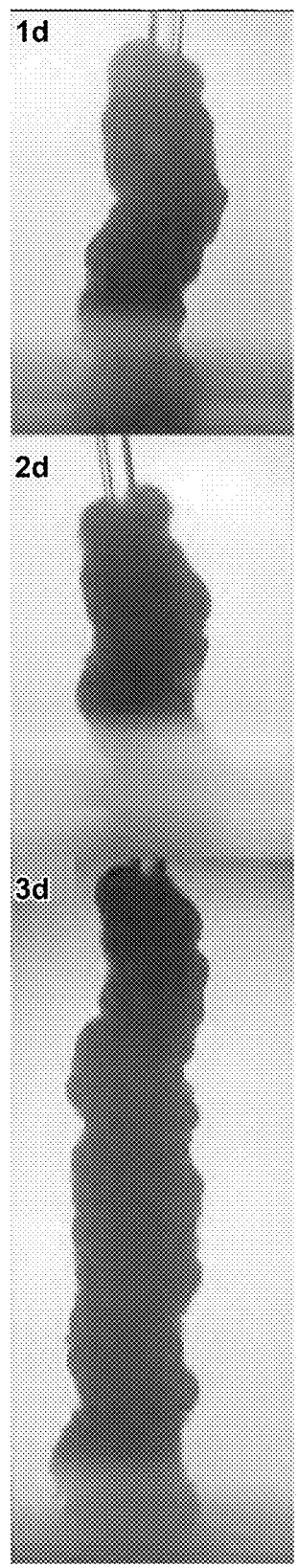
Figure 28E:
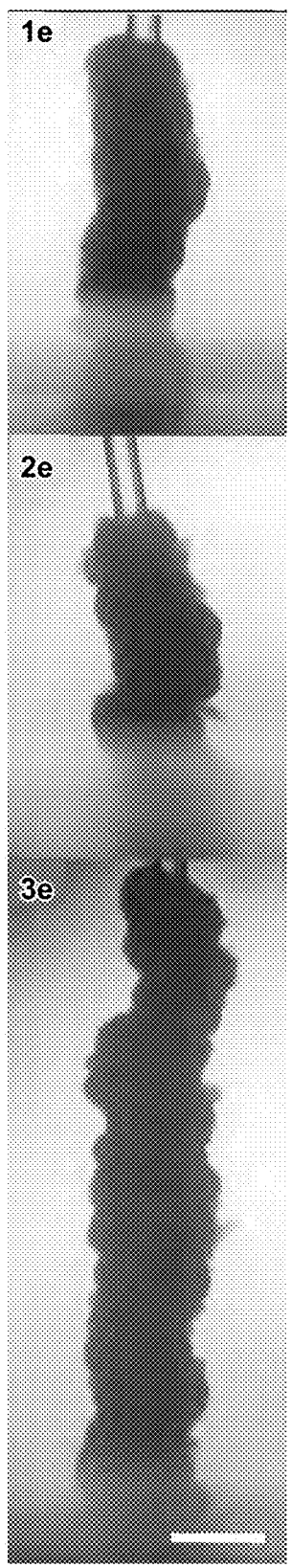

Toroids were Stacked:

To test the ability of the device to stack toroids, KGN toroids (35,000 cells/toroid) were gripped and then released over small diameter capillary tubes (330 or 170 µm outer diameter) embedded in and protruding upward from agarose. One at a time, toroids were gripped and transported so that their lumens were aligned in the x, y plane with the outer diameter of the capillary tubes. The z distance between the bio-gripper's membrane and the end of the capillary tube was approximated by observing the capillary tube catching the toroid as the tube was moved in the x, y plane relative to the toroid. Upon alignment, the toroid was released by reversal of flow through the membrane. Careful approximation of the membrane and the capillary tube in the z direction minimized occurrences of the toroid not successfully being released onto the capillary tube. By repeating this procedure, an initial stack of toroids was placed around the large diameter capillary tube (FIG. 26). The procedure was repeated with the smaller diameter capillary tube (170 μm) and taller stacks were made containing up to 16 toroids. Manual stacking of each toroid required less than 5 minutes. Stacked toroids were incubated at 37° C. and side view images taken to determine if the stacked toroids fused (FIG. 27). Over time, the toroids fused as shown by the closing of small gaps and the melding and flattening of the round edges of the toroids. The stack of toroids also contracted their lumens and appeared to attach to the capillary tube. The height of the stack of 16 toroids is greater than 3.5 mm. FIGS. 28A-28E show different toroid stacks formed by the method of the invention.

Example 2

Figures 29A, 29B, 29C, 29D:
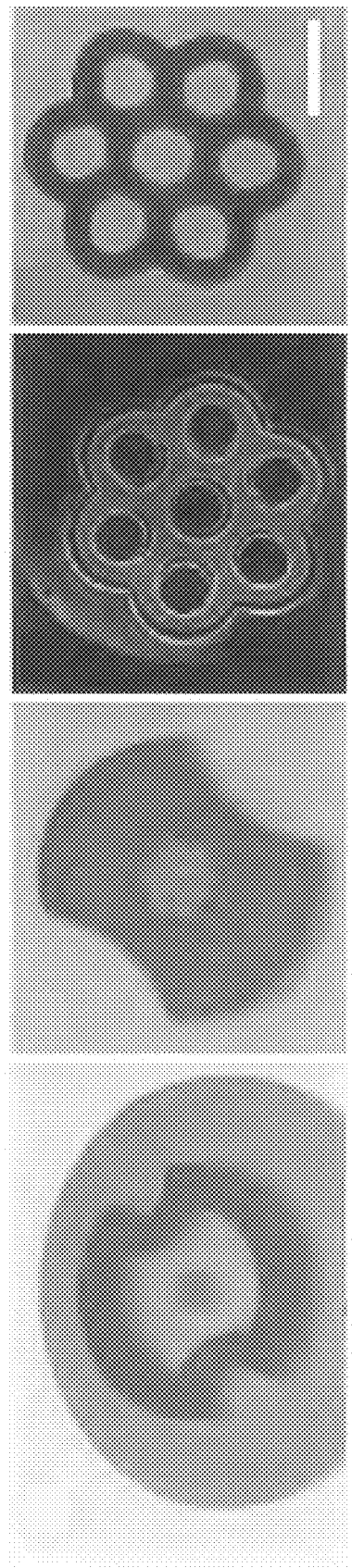
FIGS. 29A-D are a series of photographs illustrating formation of an aggregation of cells employed as a building part in another example of the invention.
Figure 30C:
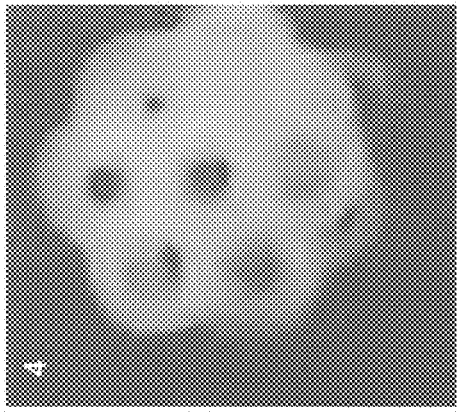
FIGS. 30A-E are a series of photographs representing assembly of building-part honeycomb microtissues (comprised of 250,000 MCF-7 cells) that were picked, placed, and stacked onto a build head by the method of the invention. Close-up overhead photos of a building sequence show a stack of two, three, and four honeycombs (FIGS. 30A, B and C, respectively). A close-up side view photo of a stack of three honeycombs on the build head is shown at the bottom left (FIG. 30D). An angled top view photo of stack of three honeycombs on a build head is shown on bottom right (FIG. 30E). The approximate time to stack four honeycombs was 15 minutes.
Figure 30E:
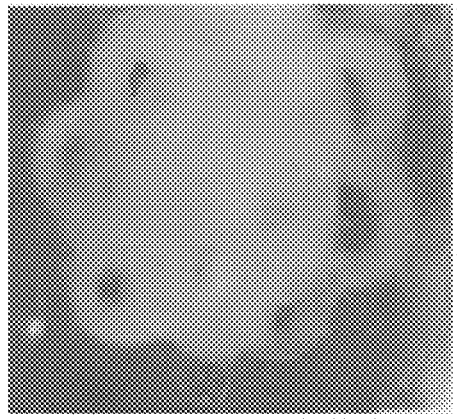
Figure 30B:
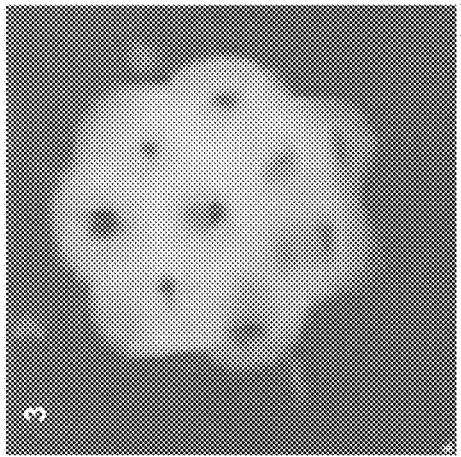
Figure 30D:
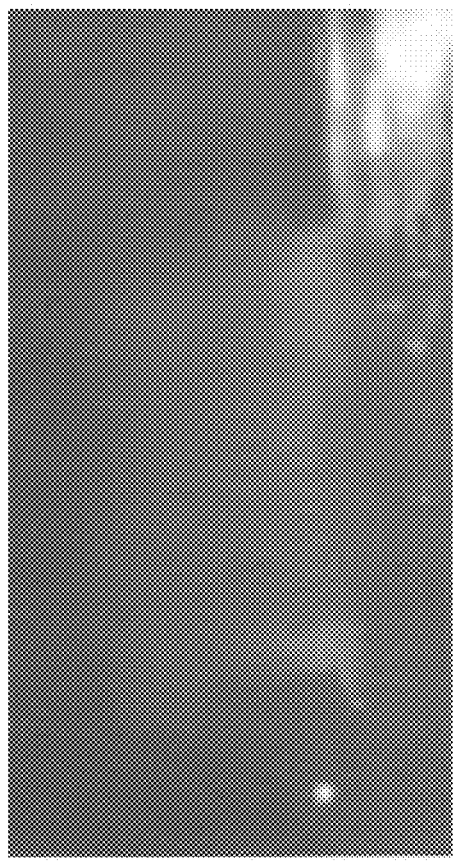
Figure 30A:
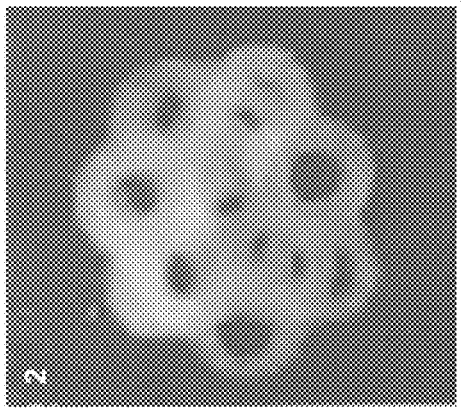

Honeycombs were gripped and stacked to determine if a device of the invention ("Bio-P3") could handle even larger and more complex building parts, we prepared multi-cellular honeycombs were prepared (FIGS. 29A-D). Shown in FIGS. 29A-D are photographs of a micro-mold (FIG. 29A) and a micro-molded agarose gel prepared from mold (FIG. 29B). After equilibration in cell culture medium, micro-molded agarose gel was seeded with 250,000 MCF-y cells that self-assembled a multi-cellular honeycomb structure in the gel within 24 hours (FIG. 29C). The cells were harvested 48 hours after seeding. Brightfield image of multi-cellular honeycomb with seven lumens after release from the gel is shown in FIG. 29D. Scale bar 500 microns. The method of preparation of multicellular honeycombs is more completely described in U.S. Pat. No. 8,361,781, the teachings of which are incorporated by reference in their entity. Honeycomb microtissues were introduced into the holding pen of the Bio-P3 instrument. They were subsequently gripped one at a time, moved into position and deposited onto the build head (FIG. 30). A stack of four honeycombs was assembled, with fair alignment of lumens through the four tissues. FIGS. 30A-E are a series of photographs representing assembly of building-part honeycomb microtissues (comprised of 250,000 MCF-7 cells) that were picked, placed, and stacked onto a build head by the method of the invention. Close-up overhead photos of a building sequence show a stack of two, three, and four honeycombs (FIGS. 30A, B and C, respectively). A close-up side view photo of a stack of three honeycombs on the build head is shown at the bottom left (FIG. 30D). An angled top view photo of stack of three honeycombs on a build head is shown on bottom right (FIG. 30E). The approximate time to stack four honeycombs was 15 minutes. This most directly demonstrates the potential of the Bio-P3 device, to assemble a large (>2 mm in smallest dimension), multi-lumen, high-density (~1 million cells total) tissue construct.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A device for assembling aggregations of adherent cells, comprising:
   a) an assembly vessel;
   b) a gripper moveable within the assembly vessel, the gripper including,
      i) a gripper housing defining a gripper chamber and at least two openings,
      ii) a gripper membrane over one of the openings,
      iii) a conduit extending from another of the openings of the gripper, and
      iv) a support at the gripper housing that controls the position of the gripper within the vessel;
   c) a perfusate source in fluid communication with the conduit extending from the gripper housing; and
   d) a build support fixed within the assembly vessel, the build support including,
      i) a build housing defining a build chamber and at least two openings,
      ii) a build membrane over one of the openings,
      iii) a conduit extending from another of the openings of the build housing to the perfusate source.

2. The device of claim 1, wherein the perfusate source includes at least one pump at the conduit extending from the gripper housing, and at the conduit extending from the opening of the build housing.

3. The device of claim 2, further including a visualization device and a controller, wherein the controller controls position of the gripper within the assembly vessel.

4. The device of claim 3, wherein the gripper has a top surface that is transparent and wherein the visualization device is fixed above the gripper.

5. The device of claim 3, wherein the assembly vessel includes a bottom portion that is essentially transparent, and wherein the visualization device is located beneath the assembly vessel.

6. The device of claim 3, wherein the vessel includes at least one side that is transparent, and wherein the visualization device is located at the side of the assembly vessel.

7. The device of claim 1, further including at least one staging support fixed within the vessel, the staging support including:
   a) a staging housing defining a staging chamber and at least two openings;
   b) a staging membrane over one of the openings; and
   c) a conduit extending from another of the openings of the staging housing to the perfusate source.

8. The device of claim 7, wherein the perfusate source includes a pump at the conduit extending from the staging housing.

9. The device of claim 8, wherein the perfusate source further includes a perfusate vessel in fluid communication with the assembly vessel.

10. The device of claim 9, further including a vessel support adjustor at the vessel, whereby actuation of the vessel support adjustor moves the vessel in a plane that is parallel to a plane defined by the gripper membrane.

11. The device of claim 10, wherein the staging membrane and the build membrane define at least one plane parallel to the plane defined by the gripper membrane.

12. The device of claim 11, wherein the membrane of the gripper defines a first surface external to the gripper chamber and the membrane of the build support defines a second surface external to the build chamber, the second surface facing a direction opposite that of the first surface.

13. The device of claim 12, further including a visualization device at the gripper and a controller, wherein the gripper support, the visualization device and the controller are linked, thereby causing elevation of the gripper to be controlled by signals from the visualization device.

14. The device of claim 13, wherein the gripper has a top portion that is transparent, the visualization device is above the gripper, and wherein the gripper membrane is transparent, whereby the visualization device can identify an aggregation of cells beneath the gripper membrane and signal identification of the aggregation of cells to the controller.

15. The device of claim 14, wherein the gripper support further includes a micromanipulator that can rotate the gripper about a longitudinal axis that is transverse to at least one plane defined by the gripper membrane, the staging membrane and the build membrane.

16. The device of claim 15, wherein the micromanipulator controls elevation of the gripper within the vessel.

17. The device of claim 16, further including a vessel support adjustor at the vessel, whereby the position of the assembly vessel is controlled in at least one plane defined by the gripper membrane, the staging membrane and the build membrane.

* * * * *